United States Patent [19]

Zimmermann et al.

[11] Patent Number: 4,497,808
[45] Date of Patent: Feb. 5, 1985

[54] N-OXIDE COMPOUNDS USEFUL IN THE TREATMENT OF CARDIOVASCULAR AILMENTS

[75] Inventors: Markus Zimmermann, Riehen; Hans Kühnis, Basel, both of Switzerland

[73] Assignee: Ciba-Geigy Corporation, Ardsley, N.Y.

[21] Appl. No.: 453,393

[22] Filed: Dec. 27, 1982

[30] Foreign Application Priority Data

Dec. 30, 1981 [CH] Switzerland .................... 8359/81
Apr. 14, 1982 [CH] Switzerland .................... 2255/82

[51] Int. Cl.³ .................. A61K 31/44; C07D 213/89; C07D 491/048
[52] U.S. Cl. .................................. 514/222; 544/58.4; 544/58.6; 544/131; 544/364; 546/116; 546/121; 546/187; 546/193; 546/194; 546/256; 546/257; 514/238; 514/252; 514/333; 514/334
[58] Field of Search .............. 546/257, 256, 116, 121, 546/187, 193, 194; 544/58.4, 58.6, 131, 364; 424/248.54, 248.55, 248.57, 250, 256, 266, 248.5, 248.51, 248.52, 246

[56] References Cited

U.S. PATENT DOCUMENTS

| | | | |
|---|---|---|---|
| 3,775,422 | 11/1973 | Bossert et al. | 294/294.9 |
| 3,862,161 | 1/1975 | Bossert et al. | 260/295.5 |
| 3,883,540 | 5/1975 | Meyer et al. | 260/294.9 |
| 3,905,983 | 9/1975 | Bossert et al. | 260/294.8 |
| 3,920,823 | 11/1975 | Meyer et al. | 424/266 |
| 3,933,834 | 1/1976 | Meyer et al. | 260/294.8 |
| 3,946,027 | 3/1976 | Bossert et al. | 260/295.5 |
| 3,966,948 | 6/1976 | Bossert et al. | 424/266 |
| 4,145,432 | 3/1979 | Sato | 424/266 |

FOREIGN PATENT DOCUMENTS 2003146 of 0000 Fed. Rep. of Germany.
2210672 of 0000 Fed. Rep. of Germany.
2228377 of 0000 Fed. Rep. of Germany.
2248150 of 0000 Fed. Rep. of Germany.
2629892 of 0000 Fed. Rep. of Germany.

Primary Examiner—Henry R. Jiles
Assistant Examiner—Bernard Dentz
Attorney, Agent, or Firm—Irving N. Feit

[57] ABSTRACT

The present invention relates to novel N-oxide compounds that have cardiovascular properties, especially antihypertensive activity, and that correspond to the formula

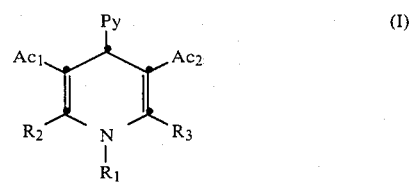

in which Py represents an unsubstituted or substituted N-oxidopyridyl radical, $R_1$ represents hydrogen or unsubstituted or substituted lower alkyl, one of the radicals $R_2$ and $R_3$ represents lower alkyl and the other represents hydrogen; lower alkyl; lower alkyl containing free, etherified or esterified hydroxy, oxo, functionally modified carboxy or free or substituted amino or imino; functionally modified carboxy; or free or substituted amino, it being possible for an amino group $R_2$ or $R_3$ to be bonded to a lower alkyl radical $R_1$ or, if $R_2$ or $R_3$ represents, for example, hydroxy-lower alkyl, for this hydroxy-lower alkyl, together with the adjacent acyl radical $Ac_1$ or $Ac_2$, to form a 2-oxa-1-oxo-lower alkylene radical, the carbonyl group of which is bonded to the 3- or 5-ring carbon atom of the 1,4-dihydropyridine ring, and each of the groups $Ac_1$ and $Ac_2$ represents, independently of the other, the acyl radical of an acid, and salts of compounds of the formula I having salt-forming groups, processes for the manufacture of these compounds, the use of these compounds and their salts, and pharmaceutical preparations which contain these compounds and salts, as antihypertensive agents and coronary dilators for the treatment of cardiovascular conditions, such as hypertonia, vascular constrictions, Angina pectoris and cardiac insufficiency.

12 Claims, No Drawings

N-OXIDE COMPOUNDS USEFUL IN THE TREATMENT OF CARDIOVASCULAR AILMENTS

The invention relates to novel N-oxide compounds and their salts and to processes for their manufacture and to pharmaceutical compositions containing them and their use.

The invention relates to compounds that correspond to the formula

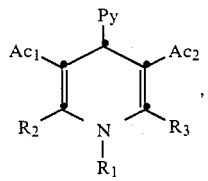

in which Py represents an unsubstituted or substituted N-oxidopyridyl radical, $R_1$ represents hydrogen or unsubstituted or substituted lower alkyl, one of the radicals $R_2$ and $R_3$ represents lower alkyl and the other represents hydrogen; lower alkyl; lower alkyl containing free, etherified or esterified hydroxy, oxo, functionally modified carboxy or free or substituted amino or imino; functionally modified carboxy; or free or substituted amino, it being possible for an amino group $R_2$ or $R_3$ to be bonded to a lower alkyl radical $R_1$ or, if $R_2$ or $R_3$ represents, for example, hydroxy-lower alkyl, for this hydroxy-lower alkyl, together with the adjacent acyl radical $Ac_1$ or $Ac_2$, to form a 2-oxa-1-oxo-lower alkylene radical, the carbonyl group of which is bonded to the 3- or 5-ring carbon atom of the 1,4-dihydropyridine ring, and each of the groups $Ac_1$ and $Ac_2$ represents, independently of the other, the acyl radical of an acid, and to salts of compounds of the formula I having salt-forming groups.

N-oxidopyridyl is N-oxido-2-pyridyl or N-oxido-4-pyridyl, but especially N-oxido-3-pyridyl, it being possible for these radicals to be unsubstituted or substituted, for example by lower alkyl, lower alkoxy, lower alkylthio, lower alkylsulphinyl, lower alkylsulphonyl or halogen.

A substituted lower alkyl radical $R_1$ contains as substituent especially unsubstituted, or more especially mono- or di-substituted, amino, such as di-lower alkylamino, N-lower alkyl-N-phenyl-lower alkylamino, or lower alkyleneamino optionally interrupted by oxygen or sulphur or by nitrogen that is unsubstituted or substituted, for example by lower alkyl; such a substituent is preferably separated from the ring nitrogen atom by at least 2 carbon atoms.

Etherified hydroxy as substituent of a lower alkyl radical $R_2$ or $R_3$ is especially lower alkoxy, while esterified hydroxy is especially halogen or lower alkanoyloxy. Functionally modified carboxy as corresponding substituent of a lower alkyl group $R_2$ or $R_3$ is especially esterified carboxy, such as lower alkoxycarbonyl, amidated carboxy, such as carbamoyl, N-lower alkylcarbamoyl or N,N-di-lower alkylcarbamoyl, or cyano. Substituted amino as substituent of lower alkyl $R_2$ or $R_3$ is mono-substituted amino, such as lower alkylamino, or preferably di-substituted amino, such as di-lower alkylamino, N-lower alkyl-N-phenyl-lower alkylamino or lower alkyleneamino optionally substituted, for example, by lower alkyl or 2-oxo-1-imidazolidinyl, and/or optionally interrupted by oxygen or sulphur or by nitrogen that is optionally substituted, for example by lower alkyl or acyl, while substituted imino is, for example, lower alkylimino, hydroxyimino or O-substituted hydroxyimino, for example lower alkoxyimino. A substituted lower alkyl radical $R_2$ or $R_3$ may contain one or more of the same or different substituents.

Functionally modified carboxy and substituted amino as the group $R_2$ or $R_3$ have, for example, the meanings given above and are especially lower alkoxycarbonyl or cyano, or lower alkylamino, di-substituted amino-lower alkylamino, such as di-lower alkylamino-lower alkylamino, or lower alkyleneamino-lower alkylamino optionally substituted in the lower alkylene moiety, for example by lower alkyl or 2-oxo-1-imidazolidinyl, and/or optionally interrupted in the lower alkylene moiety by oxygen or sulphur or by nitrogen that is optionally substituted, for example by lower alkyl or acyl, also di-lower alkylamino, or lower alkyleneamino optionally substituted in the lower alkylene moiety, for example by lower alkyl, and/or optionally interrupted in the lower alkylene moiety by oxygen or sulphur or by nitrogen that is optionally substituted, for example by lower alkyl or acyl.

An amino group bonded to a lower alkyl radical $R_1$ forms together with that radical a 1-aza-lower alkylene radical bonded via the nitrogen atom to the ring carbon atom.

An acyl radical $Ac_1$ and $Ac_2$ may represent the corresponding radical of a carboxylic acid, especially lower alkanoyl, also unsubstituted or substituted benzoyl, for example benzoyl containing lower alkyl, lower alkoxy and/or halogen, or of an organic sulpho acid, especially lower alkylsulphonyl or unsubstituted or substituted phenylsulphonyl, for example phenylsulphonyl containing lower alkyl, lower alkoxy and/or halogen. However, acyl radicals $Ac_1$ and $Ac_2$ represent more especially acyl radicals of monoesters, also monoamides, of carbonic acid, such as unsubstituted or substituted, for example free or etherified, hydroxy, such as lower alkoxy, or unsubstituted or substituted amino, such as, for example, amino described above, and especially di-substituted amino, such as di-lower alkylamino, N-lower alkyl-N-phenyl-lower alkylamino, or lower alkyleneamino optionally interrupted by oxygen or sulphur or by nitrogen that is unsubstituted or substituted, for example by lower alkyl, or lower alkoxycarbonyl containing phenyl that is unsubstituted or substituted, for example by lower alkyl, lower alkoxy and/or halogen, also N-unsubstituted or N-mono- or N,N-di-substituted carbamoyl, such as N-lower alkylcarbamoyl, N,N-di-lower alkylcarbamoyl, or N,N-lower alkylenecarbamoyl optionally interrupted in the lower alkylene moiety by oxygen or sulphur or by nitrogen that is unsubstituted or substituted, for example by lower alkyl.

The general terms used hereinbefore and hereinafter have the following meanings unless expressly defined otherwise:

The term "lower" means that groups or compounds so defined contain up to and including 7, preferably up to and including 4, carbon atoms.

Substituted radicals, especially corresponding phenyl, benzoyl, furoyl or thienoyl radicals, may contain one or more of the same or different substituents.

Lower alkyl is, for example, methyl, ethyl, n-propyl, isopropyl, n-butyl, isobutyl or tert.-butyl, also n-pentyl, n-hexyl or n-heptyl.

Lower alkoxy represents especially methoxy, ethoxy, n-propoxy, isopropoxy, n-butoxy, isobutoxy or tert.-butoxy.

Lower alkylthio is, for example, methylthio or ethylthio.

Lower alkylsulphinyl is, for example, methylsulphinyl or ethylsulphinyl.

Lower alkylsulphonyl is, for example, methylsulphonyl or ethylsulphonyl.

Halogen preferably has an atomic number of up to 35 and is especially chlorine, also fluorine or bromine, but it may also be iodine.

Di-lower alkylamino is, for example, dimethylamino, N-ethyl-N-methylamino or diethylamino.

Phenyl-lower alkyl is, for example, benzyl or 1- or 2-phenylethyl. Thus, N-lower alkyl-N-phenyl-lower alkylamino is, for example, N-benzyl-N-methylamino or N-methyl-N-(2-phenylethyl)-amino.

Lower alkyleneamino preferably contains from 4 to 6 ring carbon atoms and is, for example, pyrrolidino or piperidino, while lower alkyleneamino interrupted by oxygen may be, for example, morpholino, such as 4-morpholino, lower alkyleneamino interrupted by sulphur may be, for example, thiomorpholino, such as 4-thiomorpholino, and lower alkyleneamino interrupted by nitrogen that is optionally substituted, for example by lower alkyl, may be, for example, piperazino or 4-methylpiperazino.

Lower alkylimino is, for example, methylimino or ethylimino, while lower alkoxyimino is, for example, methoxyimino, ethoxyimino or tert.-butoxyimino.

Amino-lower alkyl groups $R_1$ are especially 2-di-substituted amino-lower alkyl, such as 2-di-lower alkylaminoethyl, for example 2-dimethylaminoethyl or 2-diethylaminoethyl, 2-lower alkyleneaminoethyl, for example 2-pyrrolidinoethyl or 2-piperidinoethyl, 2-(4-morpholino)-ethyl, or 2-(4-lower alkylpiperazino)-ethyl, for example 2-(4-methylpiperazino)-ethyl.

Lower alkanoyloxy is, for example, acetoxy or propionyloxy.

Lower alkoxycarbonyl is, for example, methoxycarbonyl, ethoxycarbonyl, n-propoxycarbonyl, isopropoxycarbonyl, n-butoxycarbonyl or tert.-butoxycarbonyl.

Phenyl-lower alkoxycarbonyl is, for example, benzyloxycarbonyl or 2-phenylethoxycarbonyl.

N-lower alkylcarbamoyl is, for example, N-methylcarbamoyl or N-ethylcarbamoyl, while N,N-di-lower alkylcarbamoyl is, for example, N,N-dimethylcarbamoyl or N,N-diethylcarbamoyl.

Lower alkylamino is, for example, methylamino, ethylamino, n-propylamino or isopropylamino.

Lower alkyleneamino substituted by 2-oxo-1-imidazolinyl is, for example, 4-(2-oxo-1-imidazolidinyl)-piperidino.

Acyl as substituent of the nitrogen atom interrupting a lower alkyleneamino radical is especially the acyl radical of a carboxylic acid, such as lower alkanoyl, for example acetyl or propionyl, benzoyl, furoyl, for example 2-furoyl, or thienoyl, for example 2-thienoyl. A corresponding aza-lower alkyleneamino radical is, for example, 4-lower alkanoylpiperazino, 4-benzoylpiperazino, 4-furoylpiperazino or 4-thienoylpiperazino.

Substituted lower alkyl radicals $R_2$ and $R_3$ are especially correspondingly substituted methyl radicals, for example hydroxymethyl, lower alkoxymethyl, halomethyl, lower alkoxycarbonylmethyl or cyanomethyl.

Di-lower alkylamino-lower alkylamino is, for example, 2-dimethylaminoethylamino, 2-diethylaminoethylamino or 3-dimethylaminopropylamino, while lower alkyleneamino-lower alkylamino correspondingly interrupted by oxygen, sulphur or optionally substituted nitrogen is, for example, 2-pyrrolidinoethylamino, 2-piperidinoethylamino, 2-(4-morpholino)-ethylamino or 2-(4-methylpiperazino)-ethylamino.

A 1-aza-lower alkylene radical that can be formed by an amino group $R_2$ or $R_3$ together with a lower alkylene radical $R_1$ is especially 1-aza-1,3-propylene, and also 1-aza-1,4-butylene; in such a radical the aza nitrogen atom is bonded to the ring carbon atom and the linking carbon atom is bonded to the ring nitrogen atom of the 1,4-dihydropyridine ring.

A 2-oxa-1-oxo-lower alkylene formed, for example, by a hydroxy-lower alkyl radical $R_2$ or $R_3$ together with the adjacent acyl radical $Ac_1$ or $Ac_2$ is especially 2-oxa-1-oxo-1,3-propylene, its 3-carbon atom being bonded to the 2- or 6-ring carbon atom and its carbonyl group being bonded to the 3- or 5-ring carbon atom of the 1,4-dihydropyridine ring.

In a substituted lower alkoxycarbonyl, the substituent is generally separated by at least 2, preferably by 2 or 3, carbon atoms from the oxygen; such radicals are, for example, hydroxy-lower alkoxycarbonyl, such as 2-hydroxyethoxycarbonyl or 2,3-di-hydroxypropoxycarbonyl, lower alkoxy-lower alkoxycarbonyl, for example 2-methoxyethoxycarbonyl, di-lower alkylamino-lower alkoxycarbonyl, for example 2-dimethylaminoethoxycarbonyl, 2-diethylaminoethoxycarbonyl or 3-dimethylaminopropoxycarbonyl, lower alkyleneamino-lower alkoxycarbonyl, for example 2-pyrrolidinoethoxycarbonyl or 2-piperidinoethoxycarbonyl, morpholino-lower alkoxycarbonyl, for example 2-(4-morpholino)-ethoxycarbonyl, or N-lower alkylpiperazino-lower alkoxycarbonyl, for example 2-(4-methylpiperazino)-ethoxycarbonyl.

N,N-lower alkylenecarbamoyl is, for example, pyrrolidinocarbonyl or piperidinocarbonyl, corresponding radicals in which the lower alkylene moiety is interrupted by oxygen, sulphur or unsubstituted or substituted nitrogen being, for example, 4-morpholinocarbonyl, 4-thiomorpholinocarbonyl, 1-piperazinocarbonyl or 4-methyl-1-piperazinocarbonyl.

Compounds of the formula I having salt-forming groups, especially corresponding basic groups, may be in the form of salts, especially acid addition salts, more especially corresponding pharmaceutically acceptable acid addition salts. Such salts are, for example, those with hydrohalic acids, for example hydrochloric acid or hydrobromic acid, also nitric acid, sulphuric acid or phosphoric acid, or organic acids, such as carboxylic acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicyclic acid, 4-aminosalicylic acid, 2-phenoxybenzoic acid, 2-acetoxybenzoic acid, embonic acid, nicotinic acid or isonicotinic acid, also amino acids, or organic sulphonic acids, such as lower alkanesulphonic acids optionally containing hydroxy, for example methanesulphonic acid, ethanesulphonic acid, 2-hydroxyethanesulphonic acid or ethane-1,2-disulphonic acid, or arylsulphonic acid, for example benzenesulphonic acid, 4-methylbenzenesulphonic acid or naphthalene-2-sulphonic acid, or other acidic organic substances, such as ascorbic acid.

Depending on the type of substitution or substituents, the compounds of the formula I may be in the form of mixtures of racemates, racemates or optically active antipodes.

The compounds of the formula I and salts of such compounds having salt-forming groups have valuable pharmacological properties, especially in the cardiovascular area. Thus, these compounds, with the exception of those in which $R_2$ or $R_3$ represents, hydroxy-lower alkyl and this hydroxy-lower alkyl, together with the adjacent acyl radical $Ac_1$ or $Ac_2$, forms a 2-oxa-1-oxo-lower alkylene radical, the carbonyl group of which is bonded to the 3- or 5-ring carbon atom of the 1,4-dihydropyridine ring, have anti-hypertensive action, as can be demonstrated, for example, in renal-hypertonic rats in accordance with the experimental procedure described by Byrom and Wilson, J. Physiol. (London), vol. 93, page 301 (1938), Gerold et al., Helv. Physiol. Pharmacol. Acta, vol. 24, page 58 (1966), and Goldblatt et al., J. Exptl. Med., vol. 59, page 347 (1934) in doses of approximately 20 mg/kg p.o. and above.

Thus, for example, a daily dose of in each case 20 mg/kg of 2,6-dimethyl-4-(1-oxido-2-methyl-2-pyridyl)-1,4-dihydropyridine-3,5-dicarboxylic acid diethyl ester administered orally over a period of 4 days to renal-hypertonic rats brings about a reduction in blood pressure of 53 mm Hg. The anti-hypertensive activity of the novel compounds can also be demonstrated in renal-hypertonic dogs in the experimental procedure of Goldblatt et al. (loc. cit.) in oral daily doses of approximately 1 mg/kg and above and in narcotised cats in the case of the intravenous administration of doses of approximately 0.01 mg/kg and above. The novel compounds of the formula I are also distinguished by the fact that, in contrast to known substances having the same direction of action and a similar structure, they have as an undesired side effect an at most marginal negatively inotropic effect. Such an effect can be detected, for example, as an inhibition of the contraction force of the isolated atrium of the guinea pig, which occurs only at relatively high concentrations, for example with an $EC_{50}$ of over 20 μmol.

The novel compounds are therefore distinguished especially by the virtual absence of undesired side effects, such as reduced cardiac output, and also by the relatively rapid onset of the pharmacological effects, by chemical stability, good solubility and, in comparison with the cardiovascular effects, by low toxicities.

The compounds of the formula I and salts of such compounds having salt-forming groups can therefore be used, for example, as antihypertensive agents and as coronary dilators, for the treatment of cardiovascular conditions, such as high blood pressure, vascular constrictions, *Angina pectoris* and its sequelae, and cardiac insufficiency.

Compounds of the formula I in which $R_2$ or $R_3$ represents, hydroxy-lower alkyl and this hydroxy-lower alkyl, together with the adjacent acyl radical $Ac_1$ and $Ac_2$, forms a 2-oxa-1-oxo-lower alkylene radical, the carbonyl group of which is bonded to the 3- or 5-ring carbon atom of the 1,4-dihydropyridine ring, bring about an increase in the myocardial contractility. This can be demonstrated in vitro, for example, on the electrically stimulated atria of guinea pigs where these preparations increase the contraction force in the concentration range of approximately 10 μmol/l and above (general information on the methodology used: J. V. Levy; Isolated atrial preparations: Methods in Pharmacology, vol. 1, Editor: H. Schwartz, pp. 77–104, Appleton-Century-Crofts, New York, 1971). Because of these effects, compounds of this type can be used for the treatment of cardiac insufficiency. The novel compounds are, however, also valuable intermediates for the manufacture of other, especially pharmaceutically active, compounds.

The invention relates especially to compounds of the formula I in which Py, $R_1$, $Ac_1$ and $Ac_2$ have the meanings given under formula I and one of the radicals $R_2$ and $R_3$ is lower alkyl and the other is hydrogen; lower alkyl; lower alkyl containing free, etherified or esterified hydroxy, functionally modified carboxy or free or substituted amino; functionally modified carboxy; or free or substituted amino, it being possible for an amino group $R_2$ or $R_3$ to be bonded to a lower alkyl radical $R_1$ or, if $R_2$ or $R_3$ represents, for example, hydroxy-lower alkyl, for this hydroxy-lower alkyl, together with the adjacent acyl radical $Ac_1$ or $Ac_2$, to form a 2-oxa-1-oxo-lower alkylene radical, the carbonyl group of which is bonded to the 3- or 5-ring carbon atom of the 1,4-dihydropyridine ring, and to salts of compounds of the formula I having salt-forming properties.

The invention relates especially to compounds of the formula I in which Py represents N-oxidopyridyl that is unsubstituted or substituted by lower alkyl, lower alkoxy, lower alkylthio, lower alkylsulphinyl, lower alkylsulphonyl and/or halogen, $R_1$ represents hydrogen, lower alkyl, di-lower alkylamino-lower alkyl, lower alkyleneamino-lower alkyl, morpholino-lower alkyl, thiomorpholino-lower alkyl, piperazino-lower alkyl or 4-lower alkylpiperazino-lower alkyl, one of the radicals $R_2$ and $R_3$ represents lower alkyl and the other represents hydrogen, lower alkyl, hydroxy-lower alkyl, lower alkoxy-lower alkyl, gem- di-lower alkoxy-lower alkyl, halo-lower alkyl, oxo-lower alkyl, lower alkoxycarbonyl-lower alkyl, carbamoyl-lower alkyl, N-lower alkylcarbamoyl-lower alkyl, N,N-di-lower alkylcarbamoyl-lower alkyl, cyano-lower alkyl, amino-lower alkyl, lower alkylamino-lower alkyl, di-lower alkylamino-lower alkyl, lower alkyleneamino-lower alkyl, morpholino-lower alkyl, thiomorpholino-lower alkyl, piperazino-lower alkyl, 4-lower alkylpiperazino-lower alkyl, lower alkoxyimino-lower alkyl, in which the lower alkoxy and imino substituents are attached to the same carbon atom, hydroxyimino-lower alkyl, lower alkoxyimino-lower alkyl, lower alkoxycarbonyl, carbamoyl, N-lower alkylcarbamoyl, N,N-di-lower alkylcarbamoyl, cyano, amino, lower alkylamino, di-lower alkylamino-lower alkylamino, lower alkyleneamino-lower alkylamino, morpholino-lower alkylamino, di-lower alkylamino, lower alkyleneamino, (2-oxo-1-imidazolidinyl)-lower alkyleneamino, morpholino, thiomorpholino, piperazino, 4-lower alkylpiperazino, 4-lower alkanoylpiperazino, 4-benzoylpiperazino, 4-furoylpiperazino or 4-thienoylpiperazino, it being possible for an amino group $R_2$ or $R_3$ also to be bonded to a lower alkyl radical $R_1$ and to form together with that radical a 1-aza-lower alkylene radical the nitrogen atom of which is bonded to the 2- or 6-ring carbon atom of the 1,4-dihydropyridine ring, or if $R_2$ or $R_3$ represents, for example, hydroxy-lower alkyl, for this hydroxy-lower alkyl, together with the adjacent acyl radical $Ac_1$ or $Ac_2$, to form a 2-oxo-1-oxo-lower alkylene radical, the carbonyl group of which is bonded to the 3- or 5-ring carbon atom of the 1,4-dihydropyridine ring, and each of the radicals $Ac_1$ and $Ac_2$, independently of the other, represents lower alkanoyl, benzoyl that is unsubstituted or substituted by lower alkyl, lower alkoxy and/or halogen, lower alkylsulphonyl, phenylsulphonyl that is unsubstituted or substituted by lower alkyl, lower alkoxy and/or halogen, lower alkoxycarbonyl, hydroxylower alkoxycarbonyl, lower alkoxy-lower alkoxycarbonyl, amino-lower alkoxycarbonyl, lower alkylamino-lower alkoxycarbonyl, di-lower alkylamino-lower alkoxycarbonyl, N-lower alkyl-N-phenyl-lower alkylamino-lower alkoxycarbonyl, lower alkyleneamino-lower alkoxycarbonyl, morpholino-lower alkoxycarbonyl, thiomorpholino-lower alkoxycarbonyl, piperazino-lower alkoxycarbonyl, 4-lower alkylpiperazino-lower alkoxycarbonyl, phenyl-lower alkoxycarbonyl that is unsubstituted or substituted by lower alkyl, lower alkoxy and/or halogen, carbamoyl, N-lower alkylcarbamoyl, N,N-di-lower alkylcarbamoyl, N,N-lower alkylenecarbamoyl, morpholinocarbonyl, thiomorpholinocarbonyl, piperazinocarbonyl or 4-lower alkylpiperazinocarbonyl, or to salts, especially pharmaceutically acceptable salts, of such compounds having salt-forming groups, especially acid addition salts, such as pharmaceutically acceptable acid addition salts, of such compounds having salt-forming basic groups.

The invention relates especially to compounds of the formula I in which Py represents N-oxidopyridyl that is unsubstituted or substituted by lower alkyl, lower alkoxy, lower alkylthio, lower alkylsulphinyl, lower alkylsulphonyl and/or halogen, $R_1$ represents hydrogen, lower alkyl, di-lower alkylamino-lower alkyl, lower alkyleneamino-lower alkyl, morpholino-lower alkyl, thiomorpholino-lower alkyl, piperazino-lower alkyl or 4-lower alkylpiperazino-lower alkyl, and one of the radicals $R_2$ and $R_3$ represents lower alkyl and the other represents hydrogen, lower alkyl, hydroxy-lower alkyl, lower alkoxy-lower alkyl, halo-lower alkyl, lower alkoxycarbonyl-lower alkyl, carbamoyl-lower alkyl, N-lower alkylcarbamoyl-lower alkyl, N,N-di-lower alkylcarbamoyl-lower alkyl, cyano-lower alkyl, amino-lower alkyl, lower alkylamino-lower alkyl, di-lower alkylamino-lower alkyl, lower alkyleneamino-lower alkyl, morpholino-lower alkyl, thiomorpholino-lower alkyl, piperazino-lower alkyl, 4-lower alkylpiperazino-lower alkyl, lower alkoxycarbonyl, carbamoyl, N-lower alkylcarbamoyl, N,N-di-lower alkylcarbamoyl, cyano, amino, lower alkylamino, di-lower alkylamino-lower alkylamino, lower alkyleneamino-lower alkylamino, morpholino-lower alkylamino, di-lower alkylamino, lower alkyleneamino, (2-oxo-1-imidazolidinyl)-lower alkyleneamino, morpholino, thiomorpholino, piperazino, 4-lower alkylpiperazino, 4-lower alkanoylpiperazino, 4-benzoylpiperazino, 4-furoylpiperazino or 4-thienoylpiperazino, it being possible for an amino group $R_2$ or $R_3$ also to be bonded to a lower alkyl radical $R_1$ and to form together with that radical a 1-aza-lower alkylene radical the nitrogen atom of which is bonded to the 2- or 6-ring carbon atom, of the 1,4-dihydropyridine ring, or, if $R_2$ or $R_3$ represents, for example, hydroxy-lower alkyl, for this hydroxy-lower alkyl, together with the adjacent acyl radical $Ac_1$ or $Ac_2$, to form a 2-oxa-1-oxo-lower alkylene radical, the carbonyl group of which is bonded to the 3- or 5-ring carbon atom of the 1,4-dihydropyridine ring, and each of the radicals $Ac_1$ and $Ac_2$, independently of the other, represents lower alkanoyl, benzoyl that is unsubstituted or substituted by lower alkyl, lower alkoxy and/or halogen, lower alkylsulphonyl, phenylsulphonyl that is unsubstituted or substituted by lower alkyl, lower alkoxy and/or halogen, lower alkoxycarbonyl, hydroxy-lower alkoxycarbonyl, lower alkoxy-lower alkoxycarbonyl, amino-lower alkoxycarbonyl, lower alkylamino-lower alkoxycarbonyl, di-lower alkylamino-lower alkoxycarbonyl, N-lower alkyl-N-phenyl-lower alkylamino-lower alkoxycarbonyl, lower alkyleneamino-lower alkoxycarbonyl, morpholino-lower alkoxycarbonyl, thiomorpholino-lower alkoxycarbonyl, piperazino-lower alkoxycarbonyl, 4-lower alkylpiperazino-lower alkoxycarbonyl, phenyl-lower alkoxycarbonyl that is unsubstituted or substituted by lower alkyl, lower alkoxy and/or halogen, carbamoyl, N-lower alkylcarbamoyl, N,N-di-lower alkylcarbamoyl, N,N-lower alkylenecarbamoyl, morpholinocarbonyl, thiomorpholinocarbonyl, piperazinocarbonyl or 4-lower alkylpiperazinocarbonyl, or to salts, especially pharmaceutically acceptable salts, of such compounds having salt-forming groups, especially acid addition salts, such as pharmaceutically acceptable acid addition salts, of such compounds having salt-forming basic groups.

The invention relates more especially to compounds of the formula I in which Py represents N-oxidopyridyl that is unsubstituted or substituted by lower alkyl or lower alkylsulphinyl, $R_1$ represents hydrogen, lower alkyl, 2-di-lower alkylamino-lower alkyl, 2-lower alkyleneamino-lower alkyl or 2-(4-morpholino)-lower alkyl, one of the radicals $R_2$ and $R_3$ represents lower alkyl and the other represents hydrogen, lower alkyl, hydroxy-lower alkyl, halo-lower alkyl, lower alkoxycarbonyl-lower alkyl, cyano-lower alkyl, di-lower alkylamino-lower alkyl, lower alkoxycarbonyl, cyano, amino, (4-morpholino)-lower alkylamino, lower alkyleneamino, (2-oxo-1-imidazolidinyl)-lower alkyleneamino or 4-(2-furoyl)-piperazino, it being possible for an amino group $R_2$ or $R_3$ to be bonded to a lower alkyl radical $R_1$ and to form together with that radical a 1-aza-lower alkylene radical, the aza nitrogen atom of which is bonded to the 2- or 6-ring carbon atom of the 1,4-dihydropyridine ring, or, if $R_2$ or $R_3$ represents, for example, hydroxy-lower alkyl, for this hydroxy-lower alkyl, together with the adjacent acyl radical $Ac_1$ or $Ac_2$, to form a 2-oxa-1-oxo-lower alkylene radical, the carbonyl group of which is bonded to the 3- or 5-ring carbon atom of the 1,4-dihydropyridine ring, and each of the radicals $Ac_1$ and $Ac_2$, independently of the other, represents lower alkanoyl, lower alkylsulphonyl, lower alkoxycarbonyl, hydroxy-lower alkoxycarbonyl, lower alkoxy-lower alkoxycarbonyl, di-lower alkylamino-lower alkoxycarbonyl, N-lower alkyl-N-phenyl-lower alkylamino-lower alkoxycarbonyl, lower alkyleneamino-lower alkoxycarbonyl, (4-morpholino)-lower alkoxycarbonyl, carbamoyl, N-lower alkylcarbamoyl, N,N-di-lower alkylcarbamoyl, N,N-lower alkylenecarbamoyl or 4-morpholinocarbonyl, wherein lower alkyl, lower alkoxy and lower alkanoyl contain up to and including 4 carbon atoms, lower alkylene contains 4 or 5 chain carbon atoms, 1-aza-lower alkylene contains 2 or 3 chain carbon atoms and 2-oxa-1-oxo-lower alkylene contains 2 chain carbon atoms, or to salts, especially pharmaceutically acceptable salts, of such compounds having salt-forming groups, especially acid addition salts, especially pharmaceutically acceptable acid addition salts, of such compounds having salt-forming basic groups.

The invention relates most especially to compounds of the formula I in which Py represents N-oxidopyridyl, especially N-oxido-3-pyridyl, $R_1$ represents, especially, hydrogen, also lower alkyl, for example methyl, 2-(di-lower alkylamino)-lower alkyl, for example dimethylaminoethyl, 2-diethylaminoethyl or 3-dimethylaminopropyl, 2-(lower alkyleneamino)-lower alkyl, for example 2-pyrrolidinoethyl or 2-piperidinoethyl, or 2-(4-morpholino)-lower alkyl, especially 2-(4-morpholino)-ethyl, one of the radicals $R_2$ and $R_3$ represents lower alkyl, especially methyl, and the other represents lower alkyl, especially methyl, hydroxy-lower alkyl, especially hydroxymethyl, halo-lower alkyl, especially chloromethyl, 2-(di-lower alkylamino)-lower alkyl, especially 2-(di-lower alkylamino)-ethyl, lower alkoxycarbonyl, especially ethoxycarbonyl, cyano, amino, (4-morpholino)-lower alkylamino, especially 2-(4-morpholino)-ethylamino, lower alkyleneamino, especially pyrrolidino, (2-oxo-1-imidazolidinyl)-lower alkyleneamino, especially 4-(2-oxo-1-imidazolidinyl)-piperidino, or 4-(2-furoyl)-piperazino, it being possible for an amino group $R_2$ or $R_3$ to be bonded to a lower alkyl radical $R_1$ and, together with that radical, to form a 1-aza-lower alkylene radical, especially 1-aza-1,3-propylene, the aza nitrogen atom of which is bonded to the 2- or 6-ring carbon atom of the 1,4-dihydropyridine ring, or, if $R_2$ or $R_3$ represents, for example, hydroxy-lower alkyl, especially hydroxymethyl, for this hydroxy-lower alkyl, together with the adjacent acyl radical $Ac_1$ or $Ac_2$, to form a 2-oxa-1-oxo-lower alkylene radical, especially 2-oxa-1-oxo-1,3-propylene, the carbonyl group of which is bonded to the 3- or 5-ring carbon atom of the 1,4-dihydropyridine ring, and each of the radicals $Ac_1$ and $Ac_2$, independently of the other, represents lower alkanoyl, for example acetyl, lower alkylsulphonyl, for example methylsulphonyl or ethylsulphonyl, lower alkoxycarbonyl, especially methoxycarbonyl, ethoxycarbonyl, n-propoxycarbonyl, isopropoxycarbonyl, n-butoxycarbonyl or isobutoxycarbonyl, 2-lower alkoxy-lower alkoxycarbonyl, especially 2-methoxyethoxycarbonyl, di-lower alkylaminolower alkoxycarbonyl, such as 2-dimethylaminoethoxycarbonyl, 2-diethylaminoethoxycarbonyl or 3-dimethylaminopropoxycarbonyl, or N-lower alkyl N-phenyl-lower alkylamino-lower alkoxycarbonyl, for example 2-(N-benzyl-N-methylamino)-ethoxycarbonyl, carbamoyl, N-lower alkylcarbamoyl, for example N-methylcarbamoyl, N,N-di-lower alkylcarbamoyl, for example N,N-dimethyl-carbamoyl, or 4-morpholinocarbonyl, wherein lower alkyl lower alkoxy and lower alkanoyl contain up to and including 4 carbon atoms, lower alkylene contains 4 or 5 chain carbon atoms, 1-aza-lower alkylene contains 2 or 3 chain carbon atoms and 2-oxa-1-oxo-lower alkylene contains 2 chain carbon atoms, or to salts, especially pharmaceutically acceptable salts, of such compounds, more especially acid addition salts, such as pharmaceutically acceptable acid addition salts, of such compounds having salt-forming basic groups.

The invention relates especially to compounds of the formula I in which Py represents N-oxidopyridyl, especially N-oxido-3-pyridyl, $R_1$ represents hydrogen, also 2-(4-morpholino)-ethyl, one of the radicals $R_2$ and $R_3$ represents methyl and the other represents, especially, methyl, also hydroxymethyl, lower alkoxycarbonyl, for example methoxycarbonyl, ethoxycarbonyl, n-propoxycarbonyl, isopropoxycarbonyl, n-butoxycarbonyl or isobutoxycarbonyl, cyano or amino, and each of the radicals $Ac_1$ and $Ac_2$, independently of the other, represents lower alkanoyl, especially acetyl, or lower alkylsulphonyl, for example ethylsulphonyl, but especially lower alkoxycarbonyl, for example methoxycarbonyl, ethoxycarbonyl, n-propoxycarbonyl, isopropoxycarbonyl, n-butoxycarbonyl or isobutoxycarbonyl, also carbamoyl, N-lower alkylcarbamoyl, for example N-methylcarbamoyl, or N,N-di-lower alkylcarbamoyl, for example N,N-dimethylcarbamoyl, wherein lower alkyl, lower alkoxy and lower alkanoyl contain up to and including 4 carbon atoms, or $R_2$ or $R_3$, as for example hydroxymethyl, together with the adjacent acyl radical $Ac_1$ or $Ac_2$, can form the 2-oxa-1-oxo-1,3-propylene radical, the carbonyl group of which is bonded to the 3- or 5-ring carbon atom of the 1,4-dihydropyridine ring, or to salts, especially pharmaceutically acceptable salts, of such compounds, more especially acid addition salts, such as pharmaceutically acceptable acid addition salts, of such compounds having salt-forming basic groups.

The invention relates especially to the specific compounds described in the Examples.

The compounds of the formula I and salts of such compounds having salt-forming groups can be manufactured in a manner known per se by, for example, (a) cyclising a compound of the formula

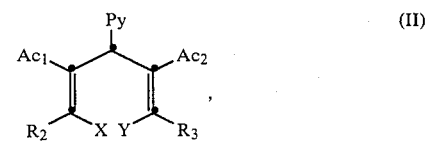

in which one of the radicals X and Y represents a group of the formula —NH—$R_1$ and the other represents hydroxy or a group of the formula —NH—$R_1$, or a tautomer thereof or a corresponding tautomeric mixture, or (b) reacting a compound of the formula Py-CHO (III) or a reactive functional derivative thereof with a compound of the formula

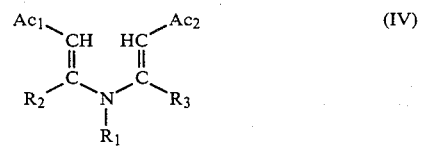

or a tautomer thereof or a corresponding tautomeric mixture, or (c) in a compound of the formula

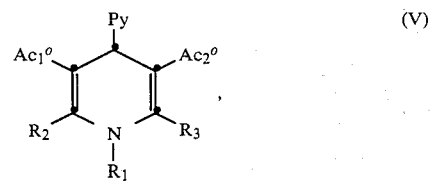

in which one of the radicals $Ac_1^o$ and $Ac_2^o$ represents a radical that can be converted into the radical $Ac_1$ or $Ac_2$ and the other represents $Ac_1$ or $Ac_2$ or a radical that can be converted into an $Ac_1$ or $Ac_2$, converting the radical $Ac_1^o$ and/or $Ac_2^o$ into a radical $Ac_1$ and/or $Ac_2$, or (d) in a compound of the formula

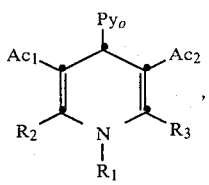  (VI)

in which $Py_o$ represents an unsubstituted or substituted pyridyl radical, oxidising the radical $Py_o$ to form the corresponding N-oxidopyridyl radical; compounds of the formula I in which $R_2$ or $R_3$, as, for example, hydroxy-lower alkyl, represents, together with the adjacent acyl radical $Ac_1$ or $Ac_2$, a 2-oxa-1-oxo-lower alkylene radical, the carbonyl group of which is bonded to the 3- or 5-ring carbon atom of the 1,4-dihydropyridine ring, can be formed directly under the reaction conditions of one of the processes (a) to (d) from starting materials of the formulae II, IV, V, and VI in which $R_2$ or $R_3$ represents lower alkyl containing free or esterified hydroxy and $Ac_1$ or $Ac_2$, or $Ac_1^o$ or $Ac_2^o$ in starting materials of the formula V, represents an esterified carboxyl group, and, in the above starting materials of the formulae II to VI, which, in so far as they have salt-forming groups, can also be used in the form of their salts, the radicals Py, $R_1$, $R_2$, $R_3$, $Ac_1$ and $Ac_2$ have the meanings given under formula I, and, if desired, a resulting compound of the formula I is converted into a different compound of the formula I, and/or, if desired, a resulting salt is converted into the free compound or into a different salt, and/or, if desired, a resulting free compound of the formula I having salt-forming groups is converted into a salt, and/or, if desired, a resulting mixture of isomers is separated into the individual isomers.

Normally, the starting materials of the formula II used in process variant (a) are formed in situ and the cyclisation according to the process can be carried out under the reaction conditions for the manufacture of the starting material. Thus, the starting materials of the formula II and, under the reaction conditions, generally also the corresponding end products of the formula I, can be obtained by (aa) reacting a compound of the formula III or a reactive functional derivative thereof with a compound of the formula

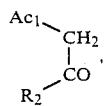  (VII)

with a compound of the formula

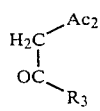  (VIII)

and with a compound of the formula $R_1$—$NH_2$ (IX), or by (ab) reacting a compound of the formula III or a reactive functional derivative thereof with a compound of the formula

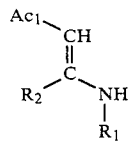  (X)

and with a compound of the formula VIII, or by (ac) reacting a compound of the formula III or a reactive functional derivative thereof with a compound of the formula

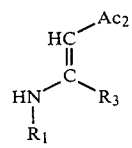  (XI)

and with a compound of the formula VII or X, or by (ad) reacting a compound of the formula IX with a compound of the formula

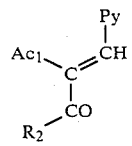  (XII)

and with a compound of the formula VIII, or by (ae) reacting a compound of the formula IX with a compound of the formula

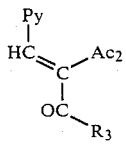  (XIII)

and with a compound of the formula VII or X, or by (af) reacting a compound of the formula IX with a compound of the formula

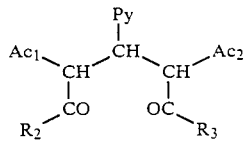  (XIV)

or by (ag) reacting a compound of the formula X with a compound of the formula XIII or the formula

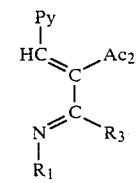  (XV)

or by (ah) reacting a compound of the formula XI with a compound of the formula XII or with a compound of the formula

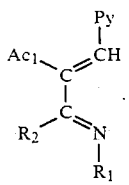

(XVI)

With the exception of the compounds of the formulae III and IX, the compounds of the formulae VII, VIII and X to XVI can be used in the form of their tautomers or in the form of mixtures of tautomers; starting materials of the above formulae having salt-forming groups can also be used in the form of salts. In addition, in the above-mentioned compounds, the groups Py, $R_1$, $R_2$, $R_3$, $Ac_1$ and $Ac_2$ have the meanings given in connection with the formula I.

Reactive functional derivatives of the aldehyde of formula III are, inter alia, the corresponding acetals, i.e. the corresponding di-(etherified hydroxy)-methyl-N-oxidopyridine compounds, such as di-lower alkyl-, for example dimethyl- or diethyl-acetals, acylals, for example the corresponding diacyloxymethyl- or dihalomethyl-N-oxidopyridine compounds, such as di-lower alkanoylacylals, for example diacetylacylals, or the corresponding dihalo, for example dichloro or dibromo, compounds, and also addition compounds, such as those with an alkali metal bisulphite, for example potassium bisulphite.

A compound of the formula IX can also be used in the form of an agent that yields that compound in situ, for example ammonia in the form of an ammonium salt, such as ammonium acetate or ammonium bicarbonate, or a light metal compound, for example an alkali metal compound, such as sodium amide or lithium N-methylamide.

The cyclisation reaction (a) and the condensation reactions (aa) to (ah) for the manufacture of the starting material, normally formed in situ, for the cyclisation reaction are variants of Hantzsch's dihydropyridine synthesis. In variant (aa), a total of three molecules of water are removed; in the other variants there is in some cases an addition reaction in the place of water removal, i.e. the water is already removed during the manufacture of one or of two starting materials. In the case of the reaction of compounds of the formula III with compounds of the formulae XI and X according to (ac), of compounds of the formula X with compounds of the formula XV according to (ag), or of compounds of the formula XI with compounds of the formula XVI according to (ah), a compound of the formula IX is removed in addition to or instead of water. If, according to variant (aa), compounds of the formula I are to be manufactured in which $R_2$ and $R_3$ and/or $Ac_1$ and $Ac_2$ differ from one another in each case, secondary products may be formed which contain the same substituents in th 3- and 5-positions and/or the 2- and 6-positions. However, by introducing the reactants at different times, the formation of such secondary products can be reduced by promoting a specific course of reaction which takes place in situ according to another variant since, in accordance with the staggered addition of the reactants, for example first of all a compound of the general formula X or of the formula XI can be formed.

The cyclisation and condensation reactions according to the process are carried out in a manner known per se, if necessary in the presence of a condensation agent, especially a basic condensation agent, such as an excess of a basic reactant or an additional, for example organic, base, such as piperidine or ethyldiisopropylamine, or a metal alcoholate, such as alkali metal-lower alkanolate, or, if a compound of the formula IX is in the form of a compound with a light metal, for example in the form of sodium amide, in the presence of acidic agents, for example an organic carboxylic acid, for example acetic acid, and/or a suitable dehydrating agent or water-absorbing agent, also customarily in the presence of an inert organic solvent and at reaction temperatures in the range of from approximately room temperature to approximately 200° C., especially at the boiling temperature of the solvent. The reaction takes place optionally in an inert gas atmosphere, for example a nitrogen atmosphere, and/or, for example when using a low-boiling solvent and/or a starting material of the formula IX, in a closed vessel under elevated pressure.

The starting materials used in the process variants are known or can be manufactured according to processes known per se.

The process variant (b) is carried out in a manner known per se. A derivative of the aldehyde of the formula III can be one of those mentioned above, for example the corresponding dihalomethyl compound. The reaction is carried out in the absence, but preferably in the presence, of a solvent or diluent or of a corresponding mixture and/or of a condensation agent, while cooling, at room temperature or, preferably, while heating, for example in a temperature range of from approximately 0° to approximately 200° C., preferably from approximately 40° to approximately 150° C., and, if necessary, in a closed vessel, optionally under pressure and/or in an inert gas atmosphere.

Starting materials of the formula IV can be obtained, for example, by reacting a 3-($R_1$-amino)-$R_2$-acrylic acid with an $R_3$-carbonylacetic acid or preferably a derivative, such as a lower alkyl ester, thereof; or alternatively a mixture of an $R_2$-carbonylacetic acid and an $R_3$-carbonylacetic acid or preferably a derivative, such as a lower alkyl ester, thereof, is reacted with an amine of the formula $R_1$—$NH_2$ (IX), it being possible to use in situ, i.e. in the reaction mixture, the starting materials formed in these cases for further reaction with the aldehyde of the formula III.

Depending on the radical(s) $Ac_1^o$ and/or $Ac_2^o$ they contain, starting materials of the formula V may be, for example, carboxylic acids ($Ac_1^o$ and/or $Ac_2^o$ are/is carboxyl), carboxylic acid anhydrides, especially mixed anhydrides, such as acid halides, for example acid chlorides or bromides ($Ac_1^o$ and/or $Ac_2^o$ are/is halocarbonyl, for example chloro- or bromo-carbonyl), also activated esters, for example cyanomethyl ester ($Ac_1^o$ and/or $Ac_2^o$ are/is cyanomethoxycarbonyl); these can be converted, optionally in the presence of condensation agents, by treatment with an alcohol, such as an unsubstituted or substituted lower alkanol, or a reactive derivative thereof, for example a corresponding alcoholate, and free carboxylic acids can also be converted by reaction with suitable diazo compounds, such as unsubstituted or substituted diazo-lower alkanes, into compounds of the formula I in which $Ac_1$ and/or $Ac_2$ represent(s) the acyl radical of a monoester of carbonic acid. Such compounds can also be obtained if salts, especially alkali metal or alkaline earth metal salts, of the free carboxylic acids are used as the starting materials and are treated with reactive esters of alcohols, such as unsubstituted or substituted lower alkanols, such as corresponding halides, for example chlorides, bromides or iodides, or organic sulphonic acid esters, for example lower alkanesulphonic acid esters or arenesulphonic acid esters, such as methanesulphonic acid esters or p-toluenesulphonic acid esters, or if corresponding hydrolysable iminoesters, such as corresponding imino-lower alkyl esters, are hydrolysed to form the esters.

The reaction of free carboxylic acids with alcohols, such as unsubstituted or substituted lower alkanols, is advantageously carried out in the presence of an acidic water-removing catalyst, such as a protonic acid, for example hydrochloric, hydrobromic, sulphuric, phosphoric or boric acid, benzenesulphonic or toluenesulphonic acid, or a Lewis acid, for example boron trifluoride etherate, in an excess of the alcohol used and/or in an inert solvent, if necessary with removal by distillation, for example azeotropic distillation, of the water liberated during the reaction. Furthermore, the reactions can also be carried out in the presence of water-binding condensation agents, such as suitably substituted carbodiimides, for example N,N'-diethyl-, N,N'-dicyclohexyl- or N-ethyl-N'-(3-dimethylaminopropyl)-carbodiimide, in inert organic solvents. Mixed anhydrides, especially acid halides, are reacted, for example, in the presence of acidbinding agents, for example organic bases, especially tertiary nitrogen bases, such as triethylamine, ethyldiisopropylamine or pyridine, or alternatively inorganic bases, for example alkali metal or alkaline earth metal hydroxides or carbonates, such as sodium, potassium or calcium hydroxide or carbonate, with alcohols or with alcoholates, for example alkali metal-lower alkanolates.

The reactions of reactive esters, for example cyanomethyl or pentachlorophenyl esters, with alcohols are carried out, for example, in a solvent that is inert towards the reactants, in a temperature range of from approximately 0° C. to approximately 120° C., preferably at from room temperature to approximately 60° C.

The hydrolysis of imidoester, especially imido-lower alkyl ester, starting materials is carried out, for example, by means of water-containing mineral acids, such as hydrochloric acid or sulphuric acid; for example, the imidoester salts, for example hydrochlorides, obtained on the addition of hydrogen chloride to nitriles and reaction with anhydrous alcohols, especially unsubstituted or substituted lower alkanols, can be hydrolysed directly to form the corresponding esters after the addition of water. The desired ester compound of the formula I can be obtained, for example, also from a mixture of nitrile, alcohol and sulphuric acid with a suitable water content without isolating the imido ester formed in situ.

Compounds of the formula I in which at least one of the radicals $Ac_1$ and $Ac_2$ represents the acyl radical of a carbonic acid monoamide can be formed from compounds of the formula V in which $Ac_1^o$ and/or $Ac_2^o$ represent(s) carboxyl groups, acid anhydride groups, such as halocarbonyl, for example chlorocarbonyl, or activated ester groups, such as cyanomethoxycarbonyl, by reacting such starting materials, optionally in the presence of a suitable condensation agent, with ammonia or an ammonia-yielding agent or an N-mono- or N-N-di-substituted amine.

These conversions of carboxy groups and suitably functionally modified reactive carboxy groups into corresponding carbamoyl groups are carried out in a manner known per se, for example in accordance with the processes described for the formation of the ester groups.

Compounds of the formula I in which at least one of the groups $Ac_1$ and $Ac_2$ represents carbamoyl can also be obtained starting from compounds of the formula V in which one of the radicals $Ac_1^o$ and $Ac_2^o$ represents cyano. Such starting materials can be converted into the desired compounds of the formula I having at least one carbamoyl group $Ac_1$ or $Ac_2$ by hydrolysis, preferably under acidic or basic conditions, for example in the presence of an alkali metal hydroxide, such as sodium hydroxide, and, if desired, of hydrogen peroxide in an aqueous-alcoholic solvent, such as aqueous ethanol.

Starting materials of the formula V having a free carboxyl group $Ac_1^o$ and/or $Ac_2^o$ can be obtained, for example, by manufacturing the corresponding 2-cyanoethyl ester, there being used, for example, in one of the processes (ab) or (ag) described above, a compound of the formula X in which $Ac_1$ is a 2-cyanoethoxycarbonyl group; for example, a 3-aminocrotonic acid 2-cyanoethyl ester optionally substituted in the amino group in accordance with the definition of $R_1$ can be reacted with the other reactants and then the resulting 2-cyanoethyl ester compound can be cleaved under mild conditions, for example by means of aqueous or aqueous-lower alkanolic 1N sodium hydroxide at room temperature, to form the free carboxylic acid. This acid can, if necessary, be converted in a manner known per se into the desired reactive functional derivatives.

The nitrile compounds of the formula V also coming into consideration as starting materials for process variant (c) can be manufactured, for example, analogously to one of process variants (aa) to (ah) by using starting materials that contain a cyano group in place of the radical $Ac_1$ and/or $Ac_2$, such as, for example, 3-aminocrotononitrile or its derivatives corresponding to the definitions of $R_1$ and/or $R_2$ instead of a compound of the formula X.

The oxidation of compounds of the formula VI according to process variant (d) to form compounds of the formula I having an N-oxidopyridyl radical can be carried out in a manner known per se, for example by treatment with organic peracids, such as lower alkane peracids or arene peracids, such as optionally suitably substituted perbenzoic acids, for example peracetic or 3-chloroperbenzoic acid, preferably at room temperature or at a reaction temperature somewhat higher than room temperature, or with aqueous hydrogen peroxide, for example at temperatures of up to 100° C., in the presence or absence of lower alkanoic acids, for example acetic acid. Care must be taken, especially when using peracids, that no over-oxidation occurs as a result of too long a reaction time.

The starting materials of the formula VI are known or can be manufactured in a manner known per se, for example in accordance with the above-mentioned process variants (a) to (c), by carrying these processes out with starting materials in which the radical Py is replaced by $Py_o$.

The above reactions can be carried out under reaction conditions known per se in the absence or, generally, presence of solvents or diluents, depending on the type of reaction and/or the reactants at reduced or elevated temperature, for example in a temperature range of from approximately −10° C. to approximately 150° C., under atmospheric pressure or in a closed vessel, optionally under pressure, and/or in an inert atmosphere, for example under a nitrogen atmosphere.

Compounds of the formula I obtainable according to the process can be converted in a manner known per se into different compounds of the formula I.

Thus, for example, an organic radical $R_1$ can be introduced into compounds of the formula I in which $R_1$ represents hydrogen by treatment with a reactive ester of an alcohol of the formula $R_1$—OH (XVII) thereby obtaining compounds of the formula I in which $R_1$ is other than hydrogen.

Reactive esters of compounds of the formula XVII, for example of unsubstituted or substituted lower alkanols, are those with strong inorganic or organic acids; there come into consideration, for example, the corresponding halides, especially chlorides, bromides or iodides, also sulphates, and lower alkanesulphonic acid esters or arenesulphonic acid esters, for example methanesulphonic acid ester, benzenesulphonic acid ester or p-toluenesulphonic acid ester. The reaction is, if necessary, carried out while cooling or heating, for example in a temperature range of from approximately 0° C. to approximately 100° C., in the presence of a suitable basic condensation agent, for example an alkali metal, an alkali metal amide or hydride or an alkali metal-lower alkoxide, such as sodium or potassium methoxide, ethoxide or tert.-butoxide, in the presence or absence of a solvent or diluent, at reduced or elevated temperature, for example in a temperature range of from approximately 0° C. to approximately 100° C., and/or under atmospheric pressure or in a closed vessel.

There are preferably used in such N-substitution reactions especially compounds of the formula I that have no hydroxy and/or other amino groups as substituents since these may possibly also react with the reactive ester of an alcohol of the formula XVII.

Furthermore, substituents present in compounds of the formula I obtainable according to the process can be converted into different substituents.

Thus, for example, esterified carboxy groups, such as corresponding groups $Ac_1$, $Ac_2$, $R_2$ and/or $R_3$ or corresponding substituents of radicals $R_2$ and/or $R_3$, can be converted into different esters by transesterification. Corresponding alcohol compounds are preferably used that have a boiling point that is clearly above that of the alcohol of the esterified group in the compound of the formula I to be converted, and the reaction is carried out, for example, in an excess of the hydroxy compound and/or in an inert organic solvent that preferably also has a boiling point clearly above that of the alcohol of the esterified group, preferably in the presence of a catalyst, for example an alkali metal-lower alkoxide, such as sodium or potassium methoxide or ethoxide, at elevated temperature and generally while distilling off the alcohol liberated.

Compounds of the formula I having esterified carboxy groups, such as lower alkoxycarbonyl groups, especially corresponding groups $Ac_1$ and/or $Ac_2$, can be converted into compounds having corresponding carboxamide groups, for example by treatment with ammonia, also with mono- or di-substituted amines, if necessary at elevated temperature and/or in a closed vessel.

Compounds of the formula I in which $R_2$ or $R_3$, together with the adjacent radical $Ac_1$ or $Ac_2$, form a 2-oxa-1-oxo-lower alkylene radical, especially a 2-oxa-1-oxo-1,3-propylene radical the carbonyl group of which is bonded to the 3- or 5-ring carbon atom of the 1,4-dihydropyridine ring, can be converted by ammonolysis or aminolysis, for example by treatment with ammonia or a mono- or di-substituted amine, into compounds of the formula I in which $R_2$ or $R_3$ represents hydroxy-lower alkyl, especially hydroxymethyl, and the corresponding adjacent group $Ac_1$ or $Ac_2$ represents an amidated carboxy group.

Compounds of the formula I in which one of the radicals $R_2$ and $R_3$, together with the adjacent radical $Ac_1$ or $Ac_2$, forms a 2-oxa-1-oxo-lower alkylene radical, especially a 2-oxa-1-oxo-1,3-propylene radical, the carbonyl group of which is bonded to the 3- or 5-ring carbon atom of the 1,4-dihydropyridine ring, can be obtained, for example, by the cyclising condensation of an optionally reactive esterified hydroxy-lower alkyl group, for example a p-tosyloxy- or acetoxy- or halo-lower alkyl group $R_2$ and/or $R_3$, with an adjacent esterified carboxy group, for example a lower alkoxycarbonyl group $Ac_1$ or $Ac_2$ in a corresponding compound of the formula I, for example at elevated temperature, for example in a range of from approximately 50° to approximately 200° C., especially at from approximately 80° to approximately 180° C.

These compounds can, however, also be obtained directly under the reaction conditions of one of the described processes (a) to (d), especially at elevated temperature, for example as indicated. If, for example, in reaction variant (ab) a starting material of the formula VIII is used in which $R_3$ represents hydroxy-lower alkyl, for example hydroxymethyl, or halo-lower alkyl, for example chloromethyl, and $Ac_2$ represents an esterified carboxy group, such as lower alkoxycarbonyl, for example methoxycarbonyl, and the reaction is carried out at elevated temperature, for example in a range of from approximately 50 to approximately 200° C., especially at from approximately 80° to approximately 180° C., compounds of the formula I can be obtained directly in which $R_3$ and $Ac_2$ together form a 2-oxa-1-oxo-lower alkylene radical, for example the 2-oxa-1-oxo-1,3-propylene radical, the carbonyl group of which is bonded to the 3-ring carbon atom of the 1,4-dihydropyridine ring.

In a compound of the formula I in which $R_2$ or $R_3$ represents hydroxy-lower alkyl, for example hydroxymethyl, hydroxy can be converted into halogen, such as chlorine, by treatment with a halogenating agent, such as a suitable inorganic or organic acid halide, for example thionyl chloride.

A compound of the formula I in which $R_2$ or $R_3$ represents halo-lower alkyl, for example chloromethyl, can be treated with a suitable cyano compound, such as a metal cyanide, for example an alkali metal cyanide, or an ammonium cyanide, to obtain a compound of the formula I in which $R_2$ or $R_3$ represents cyano-lower alkyl, for example cyanomethyl.

In a compound of the formula I in which $R_2$ or $R_3$ represents cyano or cyano-lower alkyl, the cyano group can be converted into an esterified carboxy group, such as lower alkoxycarbonyl, for example by treatment with an alcohol, such as lower alkanol, in the presence of an acid, such as a mineral acid, for example sulphuric acid, and water.

Furthermore, compounds of the formula I in which one of the radicals $R_2$ and $R_3$ represents a 2-amino-lower alkyl group, especially a 2-N,N-di-substituted aminoethyl group, can also be obtained by reacting a compound of the formula I in which one of the radicals $R_2$ and $R_3$ represents lower alkyl, especially methyl, with formaldehyde or an agent yielding formaldehyde, such as paraformaldehyde, and with an amine, especially an N,N-di-substituted amine, according to the Mannich process.

In addition, compounds of the formula I in which $R_2$ or $R_3$ represents a lower alkyl containing two lower alkoxy groups, for example methoxy or ethoxy, at the same carbon atom, especially di-lower alkoxymethyl, for example dimethoxymethyl or diethoxymethyl, can be converted into compounds of the formula I in which $R_2$ or $R_3$ represents an oxo-containing lower alkyl, especially formyl. The conversion of the ketal or acetal grouping into the free carbonyl group can be achieved in a manner known per se, for example by treatment with an acidic reagent, such as an acid, especially a mineral acid, for example hydrochloric acid, or an organic sulphonic acid, for example p-toluenesulphonic acid.

A compound of the formula I in which one of the groups $R_2$ and $R_3$ represents an oxo-containing lower alkyl, especially formyl, can be converted by reduction, for example by treatment with a suitable hydride reducing agent, such as an alkali metal borohydride, for example sodium borohydride, into a compound of the formula I in which $R_2$ or $R_3$ represents hydroxy-lower alkyl, especially hydroxymethyl. It can also be converted by treatment with an optionally O-substituted hydroxyamine, such as lower alkoxyamine, or an acid addition salt thereof, into a compound of the formula I in which $R_2$ or $R_3$ represents a lower alkyl containing optionally O-substituted hydroxyimino, especially optionally O-substituted hydroxyiminomethyl.

In a compound of the formula I in which $R_2$ or $R_3$ represents a lower alkyl containing optionally O-substituted hydroxyimino, this lower alkyl can be converted by reduction, for example by treatment with a suitable hydride reducing agent, such as an alkali metal borohydride, for example sodium cyanoborohydride, into a lower alkyl containing optionally N-mono-substituted amino. A compound of the formula I having a hydroxyimino-lower alkyl group, especially a hydroxyiminomethyl group, as $R_2$ or $R_3$ can be converted by dehydration, for example by treatment with an inorganic acid halide, such as phosphorus oxychloride, or a carbodiimide compound, such as N,N'-dicyclohexyl carbodiimide, into a compound of the formula I in which $R_2$ or $R_3$ represents cyano or cyano-lower alkyl.

Depending on the reaction conditions, the compounds of the formula I can be obtained in free form or in the form of salts.

Resulting acid addition salts can be converted in a manner known per se into the free compounds, for example by treatment with a base, such as an alkali metal hydroxide, or into different salts, for example by treatment with suitable acids or derivatives thereof. Resulting free compounds having salt-forming groups, for example having corresponding basic groups, can be converted into their salts, for example by treatment with acids or corresponding anion exchangers.

As a result of the close relationship between the compounds of the formula I in free form and in the form of salts, hereinbefore and hereinafter the free compounds and their salts shall be understood to mean optionally also the corresponding salts and free compounds, respectively, where appropriate with regard to meaning and purpose.

The compounds, including their salts, can also be obtained in the form of their hydrates, or their crystals may include, for example, the solvent used for crystallisation.

Depending upon the process reaction and/or the type of starting materials, the compounds of the formula I can be obtained in the form of racemates or racemic mixtures or optical antipodes.

Resulting racemic mixtures can be separated into the pure racemates or diastereoisomers in known manner, on the basis of the physico-chemical differences between the constituents, for example by chromatography and/or fractional crystallisation.

Racemates can be separated into the optical antipodes according to methods known per se, for example by recrystallisation from an optically active solvent, with the aid of suitable micro-organisms or by reaction of a compound of the formula I having salt-forming, for example basic, groups, with an optically active salt-forming agent, such as an optically active acid, and separating the mixtures of salts obtained in this manner, for example on the basis of their differing solubilities, into the diastereoisomeric salts, from which the antipodes can be freed, for example by treatment with a base.

Optical antipodes of neutral compounds of the formula I can be obtained, for example, also according to process (c) using an optically active acid of the formula V which can be formed, for example, from the corresponding racemic acid in customary manner, for example by salt formation with an optically active base, separating the diastereoisomeric salts and liberating the optically active acid, or using a reactive functional derivative of an optically active acid.

It is also possible, for example, to transesterify compounds of the formula I that have an esterified carboxy group, for example a corresponding group $Ac_1$ or $Ac_2$, using an optically active alcohol according to the process described above, and to separate the resulting mixture of diastereoisomers into the antipodes, for example by means of fractional crystallisation.

Advantageously, the pharmacologically more active isomer or the more active antipode is isolated from the mixture of diastereoisomers or the racemate.

The invention relates also to those embodiments of the process according to which a compound obtainable as an intermediate at any stage of the process is used as starting material and the remaining steps are carried out, or a starting material is used in the form of a derivative, for example a salt, and/or a racemate or antipode, or is formed under the reaction conditions.

The starting materials used in the processes of the present invention are preferably those which result in the compounds described at the beginning as being especially valuable. The present invention relates also to novel starting materials and to processes for their manufacture. The invention relates also to novel intermediates obtainable according to the processes, and to processes for their manufacture.

The invention relates also to the use of the compounds of the formula I or pharmaceutically acceptable salts of such compounds having salt-forming groups, especially as compounds that are pharmacologically active, especially in the cardiovascular area. They can be used, preferably in the form of pharmaceutical preparations, in a method for the prophylactic and/or therapeutic treatment of hypertonia, on the one hand, and of other cardiovascular diseases, for example cardiac insufficiency, on the other. The dosage of the active ingredient, which is administered alone or together with the customary carriers and adjuncts, depends on the species to be treated, age and individual condition, and on the method of administration. The daily doses of the antihypertensively active compounds are, for mammals having a body weight of approximately 70 kg, depending on the nature of the illness, individual condition and age, preferably between 5 and 200 mg, while the daily individual doses of the compounds increasing the myocardial contractility are within a range of from approximately 100 to 600 mg.

The invention further relates to pharmaceutical preparations that contain as active ingredients compounds of the formula I or pharmaceutically acceptable salts of such compounds having salt-forming groups, and also to processes for their manufacture.

The pharmaceutical preparations according to the invention are for enteral, such as peroral or rectal, and also for sublingual and parenteral administration to warm-blooded animals. Appropriate dosage unit forms, especially for peroral and/or sublingual administration, for example dragées, tablets or capsules, contain preferably from approximately 2.5 to approximately 100 mg, especially from approximately 5 to approximately 25 mg, of a compound of the formula I or a pharmaceutically acceptable salt of a corresponding compound that is capable of salt formation, together with pharmaceutically acceptable carriers.

Suitable carriers are especially fillers, such as sugar, for example lactose, saccharose, mannitol or sorbitol, cellulose preparations and/or calcium phosphates, for example tricalcium phosphate or calcium biphosphate, also binders, such as starch pastes using, for example, corn, wheat, rice or potato starch, gelatine, tragacanth, methylcellulose and/or, if desired, disintegrators, such as the above-mentioned starches, also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores are provided with suitable coatings that are optionally resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Dyes or pigments can be added to the tablets or dragée coatings, for example for identification purposes or to indicate different doses of active ingredient.

Further pharmaceutical preparations for oral administration are dry-filled capsules consisting of gelatine and also soft sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers. Preferred are, inter alia, capsules which can both be chewed slightly in order to achieve as rapid an effect as possible by sublingual absorption of the active ingredient, for example on the first signs of an attack of *Angina pectoris*, and which can also be swallowed unchewed.

As rectally administrable pharmaceutical preparations there come into consideration, for example, suppositories which consist of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base materials there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that contain substances which increase the viscosity, for example sodium carboxymethyl-cellulose, sorbitol and/or dextran, and, optionally, stabilisers.

The pharmaceutical preparations of the present invention can be manufactured in a manner known per se, for example by means of conventional mixing, granulating, confectioning, dissolving or lyophilising processes. For example, pharmaceutical preparations for oral use can be obtained by combining the active ingredient with solid carriers, optionally granulating a resulting mixture and processing the mixture or granulate, if desired or necessary after the addition of suitable adjuncts, to form tablets or dragée cores.

The following Examples illustrate the invention described above but do not limit its scope in any way. Temperatures are given in degrees Centigrade.

EXAMPLE 1

A mixture of 12.4 g of pyridine-3-carboxaldehyde-1-oxide, 17.3 ml of methyl acetoacetate, 16 ml of absolute ethanol and 8 ml of 30% aqueous ammonia is stirred at a bath temperature of 100° for 2 hours. After cooling, 100 ml of water are slowly added dropwise and the reaction mixture is concentrated under reduced pressure (water jet vacuum). A precipitate forms which, when recrystallised from isopropanol, yields 2,6-dimethyl-4-(1-oxido-3-pyridyl)-1,4-dihydropyridine-3,5-dicarboxylic acid dimethyl ester and melts at 222°–224°. The pyridine-3-carboxaldehyde-1-oxide is produced in accordance with the process described in Z. Chem., vol. 10, page 184 (1970).

EXAMPLE 2

A mixture of 18.4 g of pyridine-3-carboxaldehyde-1-oxide, 24 ml of absolute ethanol, 38.1 ml of ethyl acetoacetate and 15 ml of 30% aqueous ammonia is heated for 1¾ hours at a bath temperature of 100°, then cooled, and 144 ml of water are added dropwise thereto. The resulting suspension is stirred at room temperature for approximately one hour and the precipitate is filtered off. The resulting 2,6-dimethyl-4-(1-oxido-3-pyridyl)-1,4-dihydropyridine-3,5-dicarboxylic acid diethyl ester melts at 191°–192° after recrystallisation from 240 ml of acetonitrile.

EXAMPLE 3

11 ml of methyl acetoacetate and 13.7 g of 3-aminocrotonic acid ethyl ester are added to a mixture of 12.3 g of pyridine-3-carboxaldehyde-1-oxide in 120 ml of absolute ethanol and the reaction mixture is heated at a bath temperature of 90°. After a short time, a clear solution is obtained; after heating for 3½ hours at this temperature, the reaction mixture is concentrated by evaporation under a water jet vacuum. The oily residue is stirred with 200 ml of water, whereupon a crystalline product precipitates. This is filtered off, washed with water, dried over phosphorus pentoxide and recrystallised from acetonitrile. The resulting 2,6-dimethyl-4-(1-oxido-3-pyridyl)-1,4-dihydropyridine-3-carboxylic acid methyl ester 5-carboxylic acid ethyl ester melts at 183°–185°.

EXAMPLE 4

A mixture of 6.15 g of pyridine-3-carboxaldehyde-1-oxide, 8.7 g of acetoacetic acid isobutyl ester, 6.5 g of 3-aminocrotonic acid methyl ester and 5 g of molecular sieve (Union Carbide, 3 Å) in 50 ml of absolute ethanol is heated at a bath temperature of 90° for 4 hours. After cooling, the molecular sieve is filtered off and the filtrate is concentrated to dryness by evaporation under reduced pressure. The residue is partitioned between 50 ml of diethyl ether and 50 ml of 2N hydrochloric acid; after shaking thoroughly, the layers are separated and the organic phase is washed twice with 50 ml of 2N hydrochloric acid each time. The combined hydrochloric acid solutions are treated with activated carbon and filtered, 20 g of potassium bicarbonate are added to the filtrate and then extraction is carried out with ethyl acetate. The organic extract is dried over sodium sulphate and concentrated by evaporation, and the residue is stirred with 40 ml of boiling acetonitrile, then filtered. The filtrate is concentrated to dryness by evaporation under reduced pressure and the residue is recrystallised by dissolving in 60 ml of ethyl acetate and diluting with 30 ml of diethyl ether. The resulting 2,6-dimethyl-4-(1-oxido-3-pyridyl)-1,4-dihydropyridine-3-carboxylic acid isobutyl ester 5-carboxylic acid methyl ester melts at 139°–144°. The compound is chromatographed over silica gel using as eluant a mixture of ethyl acetate/hexane/methanol (10:20:5), after which the fractions containing the desired compound are worked up to produce the compound in pure form with a melting point of 155°–156.5°.

EXAMPLE 5

Analogously to the process described in Example 1 there is obtained from 24.1 g of 2-methylpyridine-6-carboxaldehyde-1-oxide, 40 ml of ethanol, 50.4 ml of ethyl acetoacetate and 20 ml of 25% aqueous ammonia, 2,6-dimethyl-4-(2-methyl-1-oxido-6-pyridyl)-1,4-dihydropyridine-3,5-dicarboxylic acid diethyl ester which, after recrystallisation from ethanol, melts at 224°–225° (with decomposition).

The 2-methylpyridine-6-carboxaldehyde-1-oxide used as starting material can be produced analogously to the process described in J. Org. Chem., vol. 40, page 1391 (1975) by heating a mixture of 24.6 g of 2,6-lutidine-1-oxide and 26.6 g of selenium dioxide in 160 ml of pyridine for 20 hours at a bath temperature of 125°; the crude product is further processed without being further purified.

EXAMPLE 6

A mixture of 12.3 g of pyridine-3-carboxaldehyde-1-oxide, 100 ml of ethanol, 10 g of molecular sieve (Union Carbide, 3 Å) and 12.6 ml of ethyl acetoacetate stirred at room temperature for 2 hours and then 24 g of 3-[2-(4-morpholino)-ethylamino]-crotonic acid ethyl ester in 20 ml of ethanol are added. The reaction mixture is heated at a bath temperature of 90° for 3 hours while stirring, then filtered, and the filtrate has added to it 40 ml of a 3N solution of hydrogen chloride in diethyl ether. Stirring is carried out for one hour, the precipitate is filtered off (and discarded) and the filtrate is treated again with 20 ml of the 3N solution of hydrogen chloride in diethyl ether. The resulting precipitate is filtered off and dissolved in water; 10 g of potassium bicarbonate are added to the solution and extraction is carried out with ethyl acetate. The organic extract is concentrated to dryness by evaporation and the crystalline residue is recrystallised from 1,2-dimethoxyethane. The 2,6-dimethyl-1-[2-(4-morpholino)-ethyl]-4-(1-oxido-3-pyridyl)-1,4-dihydropyridine-3,5-dicarboxylic acid diethyl ester melts at 142°–144°.

EXAMPLE 7

A solution of 2.1 g of 3-chloroperbenzoic acid in 40 ml of methylene chloride is added dropwise to a mixture of 3.3 g of 2,6-dimethyl-4-(3-pyridyl)-1,4-dihydropyridine-3,5-dicarboxylic acid diethyl ester and 1.4 g of sodium acetate in 50 ml of methylene chloride. The reaction mixture is stirred at room temperature for 20 hours and extracted with a 2N aqueous sodium carbonate solution and then twice with an aqueous iron(II) sulphate solution. The organic solution is dried and concentrated by evaporation under reduced pressure. The residue is chromatographed over 400 g of silica gel, there being used as liquid phase a 95:5 mixture of chloroform and methanol and the chromatograph being effected by means of thin layer chromatography (silica gel; mobile phase: chloroform/methanol 95:5). The eluate, which contains the main portion of the desired compound, is concentrated by evaporation, and the residue is crystallised from acetonitrile. In this manner, 2,6-dimethyl-4-(1-oxido-3-pyridyl)-1,4-dihydropyridine-3,5-dicarboxylic acid diethyl ester is obtained, which melts at 191°–193° and is identical to the product obtainable in accordance with the process of Example 2.

EXAMPLE 8

A mixture of 22.5 g of 1-methylsulphonyl-1-(1-oxido-3-pyridylmethylene)-acetone, 16.5 g of 3-aminocrotonic acid methyl ester and 45 g of molecular sieve (Union Carbide, 3 Å) in 250 ml of absolute ethanol is boiled under reflux for 18 hours. The resulting suspension is filtered, the filter residue is washed with chloroform and the filtrate is concentrated by evaporation under reduced pressure. The oily residue is dried by the addition of toluene and renewed concentration by evaporation under reduced pressure. The residue is chromatographed over approximately 50 to 100 times the amount of silica gel, a mixture of chloroform and methanol (9:1) being used as the liquid phase. Once the starting materials and intermediate have been removed by washing, the desired product is eluted; the corresponding fractions are combined and concentrated by evaporation and the residue is recrystallised from a mixture of isopropanol and diethyl ether. In this manner 2,6-dimethyl-5-methylsulphonyl-4-(1-oxido-3-pyridyl)-1,4-dihydropyridine-3-carboxylic acid methyl ester having a melting point of 236°–238° is obtained.

The starting material can be obtained in the following manner: A mixture of 6.15 g of pyridine-3-carboxaldehyde-1-oxide, 6.8 g of methylsulphonyl acetone and 1 ml of piperidine in 20 ml of dimethylformamide and 400 ml of absolute benzene is heated under reflux with removal of water formed, and then concentrated by evaporation under reduced pressure; the final remains of dimethylformamide are removed by the addition of toluene and renewed concentration by evaporation under reduced pressure. The residue, containing the crude 1-methylsulphonyl-1-(1-oxido-3-pyridylmethylene)-acetone, is used without being further purified.

EXAMPLE 9

A mixture of 10.9 g of pyridine-3-carboxaldehyde-1-oxide and 11.4 g of 3-aminocrotonic acid ethyl ester, 14.57 g of 4-chloroacetic acid ethyl ester and 10.0 g of molecular sieve (Union Carbide, 3 Å) in 50 ml of absolute ethanol is heated under reflux for 15 hours. The resulting suspension is filtered, the residue from filtration is washed with chloroform and the filtrate is concentrated by evaporation under reduced pressure. The oily residue is dried by the addition of toluene and renewed concentration by evaporation under reduced pressure, and chromatographed over approximately 50 to 100 times the amount of silica gel using a mixture of chloroform and methanol (9:1) for elution. The uniform fractions ascertained by means of thin layer chromatography are combined and concentrated to dryness by evaporation, and the residue is recrystallised from methanol. The resulting 2-methyl-4-(1-oxido-3-pyridyl)-5-oxo-1,4,5,7-tetrahydrofuro[3,4-b]pyridine-3-carboxylic acid ethyl ester of the formula

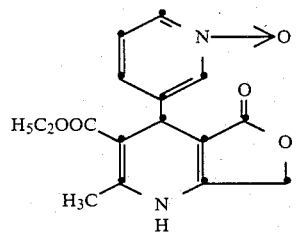

melts at 253°–255°; it is formed under the reaction conditions from the 6-chloromethyl-2-methyl-4-(1-oxido-3-pyridyl)-1,4-dihydropyridine-3,5-dicarboxylic acid diethyl ester formed as intermediate.

EXAMPLE 10

A mixture of 10.0 g of 2-methyl-4-(1-oxido-3-pyridyl)-5-oxo-1,4,5,7-tetrahydrofuro[3,4-b]pyridine-3-carboxylic acid ethyl ester and 100 ml of a 33% solution of methylamine in ethanol is heated at 90° in a sealed tube for 16 hours. The reaction mixture is concentrated to dryness by evaporation under reduced pressure and the residue is partitioned between methylene chloride and a 2N aqueous sodium carbonate solution. The organic phase is removed, washed with water, dried and concentrated by evaporation under reduced pressure. The residue is chromatographed over silica gel and eluted with ethyl acetate. The uniform fractions ascertained by means of a thin layer chromatograph are concentrated to dryness by evaporation under reduced pressure and the residue is recrystallised from a mixture of isopropanol and petroleum ether to yield 6-hydroxymethyl-2-methyl-5-methylaminocarbonyl-4-(1-oxido-3-pyridyl)-1,4-dihydropyridine-3-carboxylic acid ethyl ester melting at 197°.

EXAMPLE 11

Analogously to the process described in Example 1 there is obtained from 22.5 g of pyridine-2-carboxaldehyde-1-oxide, 37 ml of ethyl acetoacetate and 14.5 ml of 30% aqueous ammonia in 29 ml of absolute ethanol, 2,6-dimethyl-4-(1-oxido-2-pyridyl)-1,4-dihydropyridine-3,5-dicarboxylic acid dietyl ester which, after recrystallisation from 250 ml of acetonitrile, melts at 198°–200°.

The pyridine-2-carboxaldehyde-1-oxide used as starting material can be produced, for example, in accordance with the process described in Z. Chem., vol. 10, page 184 (1970).

EXAMPLE 12

Analogously to the process described in Example 1 there is obtained from 12.3 g of pyridine-4-carboxaldehyde-1-oxide, 25.7 ml of ethyl acetoacetate and 10 ml of 30% aqueous ammonia in 20 ml of absolute ethanol, 2,6-dimethyl-4-(1-oxido-4-pyridyl)-1,4-dihydropyridine-3,5-dicarboxylic acid diethyl ester which, after recrystallisation from 100 ml of isopropanol, melts at 229°–231°.

The pyridine-4-carboxaldehyde-1-oxide used as starting material can be produced, for example, in accordance with the process described in Z. Chem., vol. 10, page 184 (1970).

EXAMPLE 13

Analogously to the process described in Example 1 there is obtained from 12.3 g of pyridine-3-carboxaldehyde-1-oxide, 28.8 g of acetoacetic acid n-propyl ester and 10 ml of 30% aqueous ammonia in 20 ml of absolute ethanol, 2,6-dimethyl-4-(1-oxido-3-pyridyl)-1,4-dihydropyridine-3,5-dicarboxylic acid di-n-propyl ester which, after recrystallisation from 125 ml of acetonitrile, melts at 190°–192°.

EXAMPLE 14

Analogously to the process described in Example 1 there is obtained from 8.4 g of 2-methylpyridine-3-carboxaldehyde-1-oxide, 16.5 ml of ethyl acetoacetate and 6.1 ml of 30% aqueous ammonia in 34 ml of absolute ethanol, 2,6-dimethyl-4-(2-methyl-1-oxido-3-pyridyl)-1,4-dihydropyridine-3,5-dicarboxylic acid diethyl ester which, after recrystallisation from 600 ml of acetonitrile, melts at 228°–230°.

The 2-methylpyridine-3-carboxaldehyde-1-oxide used as starting material can be produced, for example, in accordance with the process described in Z. Chem., vol. 10, pages 184 (1970).

EXAMPLE 15

Analogously to the process described in Example 1 there is obtained from 8.4 g of 2-chloropyridine-3-carboxaldehyde-1-oxide, 12.75 ml of ethyl acetoacetate and 5 ml of 30% aqueous ammonia in 35 ml of absolute ethanol, 2,6-dimethyl-4-(2-chloro-1-oxido-3-pyridyl)-1,4-dihydropyridine-3,5-dicarboxylic acid diethyl ester which, after recrystallisation from 500 ml of isopropanol, melts at 255°–256°.

The 2-chloropyridine-3-carboxaldehyde-1-oxide used as starting material can be produced, for example, in accordance with the process described in Z. Chem., vol. 10, page 184 (1970).

EXAMPLE 16

A mixture of 14.7 g of pyridine-3-carboxaldehyde-1-oxide, 17.3 g of acetoacetic acid isopropyl ester and 12 g of molecular sieve (Union Carbide 3 Å) in 145 ml of absolute ethanol is stirred at room temperature for 2 hours. Subsequently, 19 g of 3-aminocrotonic acid (2-methoxyethyl)-ester are added and the mixture is heated at a bath temperature of 90° for 3 hours. The cooled reaction mixture is filtered, the molecular sieve is washed with ethanol and the combined filtrates are concentrated by evaporation under reduced pressure; the oily residue crystallises after the addition of acetonitrile. The crude product is filtered off and recrystallised first from 620 ml of ethyl acetate using an activated carbon preparation and then from 110 ml of acetonitrile. In this manner 2,6-dimethyl-4-(1-oxido-3-pyridyl)-1,4-dihydropyridine-3-carboxylic acid isopropyl ester 5-carboxylic acid (2-methoxyethyl)-ester having a melting point of 181°–183° is obtained.

EXAMPLE 17

A mixture of 12.3 g of pyridine-3-carboxaldehyde-1-oxide, 10 g of molecular sieve (Union Carbide, 3 Å) and 24.9 g of acetoacetic acid [2-(N-methyl-N-benzylamino)-ethyl]-ester in 120 ml of absolute ethanol is heated for 1 hour at a bath temperature of 90°. It is allowed to cool, then 11.9 g of 3-aminocrotonic acid methyl ester are added and the mixture is heated again for 3 hours at a bath temperature of 90°. The reaction mixture is filtered at room temperature, the residue from filtration (molecular sieve) is washed with ethanol and the combined filtrates are concentrated by evaporation under reduced pressure. The residue is dissolved in 310 ml of ethyl acetate, the small quantity of insoluble material is filtered off and the solution is extracted twice with 100 ml of 2N hydrochloric acid each time. The aqueous phase is rendered basic by the addition of potassium carbonate and extracted three times with 100 ml of ethyl acetate each time. The combined organic extracts are washed with saturated aqueous potassium bicarbonate solution, then with water, and finally with a saturated aqueous sodium chloride solution, and dried over sodium sulphate. After filtration and concentration by evaporation a glutinous residue remains, which is chromatographed over 1200 g of silica gel 60 (particle size 0.063–0.2 mm) using methylene chloride with increasing proportions of methanol (1%, 7% and 10%). The fractions containing the desired product are ascertained by means of thin layer chromatography, combined and concentrated by evaporation under reduced pressure. The residue is stirred with 20 ml of tert.-butyl methyl ether at room temperature, filtered and recrystallised from 110 ml of dimethoxyethane using an activated carbon preparation. In this manner 2,6-dimethyl-4-(1-oxide-3-pyridyl)-1,4-dihydropyridine-3-carboxylic acid methyl ester 5-carboxylic acid [2-(N-methyl-N-benzylamino)-ethyl]-ester having a melting point of 147°–149° is obtained.

EXAMPLE 18

A mixture of 12.3 g of pyridine-3-carboxaldehyde-1-oxide and 12.9 g of 3-aminocrotonic acid ethyl ester, 14.6 g of 4-methoxyacetoacetic acid methyl ester and 25.0 g of molecular sieve (Union Carbide, 3 Å) in 100 ml of absolute ethanol is heated under reflux for 19 hours. The resulting suspension is filtered, the residue from filtration is washed with chloroform and the filtrate is concentrated by evaporation under reduced pressure. The oily residue is dried by the addition of toluene and renewed concentration by evaporation under reduced pressure and chromatographed over approximately 50 to 100 times the amount of silica gel, elution being carried out with a mixture of chloroform and methanol (9:1). The uniform fractions ascertained by means of thin layer chromatography are combined and concentrated to dryness by evaporation, and the residue is recrystallised from a mixture of isopropanol and petroleum ether. The resulting 6-methoxymethyl-2-methyl-4-(1-oxido-3-pyridyl)-1,4-dihydropyridine-3-carboxylic acid ethyl ester 5-carboxylic acid methyl ester melts at 165°–167°.

EXAMPLE 19

A mixture of 12.3 g of pyridine-3-carboxaldehyde-1-oxide, 12.8 g of amidinoacetic acid ethyl ester and 13.0 g of ethyl acetoacetate in 500 ml of absolute ethanol is heated under reflux for 11 hours and the resulting solution is concentrated by evaporation under reduced pressure. The oily residue is dried by the addition of toluene and renewed concentration by evaporation under reduced pressure, then dissolved in ethyl acetate and the solution is extracted several times with 2N hydrochloric acid. The combined acidic extracts are rendered basic with a concentrated aqueous ammonia solution and extracted with ethyl acetate. After drying and concentration by evaporation, the residue is chromatographed over 50 to 100 times the amount of silica gel, elution being carried out with a mixture of chloroform and methanol (9:1). The uniform fractions ascertained by means of thin layer chromatography are combined and concentrated to dryness by evaporation, and the residue is recrystallised from a mixture of ethanol and diethyl ether. The resulting 2-amino-6-methyl-4-(1-oxido-3-pyridyl)-1,4-dihydropyridine-3,5-dicarboxylic acid diethyl ester melts at 232°–234°.

EXAMPLE 20

Analogously to the method described in Example 1 there is obtained from 4.1 g of 2-methylthiopyridine-3-carboxaldehyde-1-oxide, 6.45 g of ethyl acetoacetate and 2.45 ml of 30% aqueous ammonia in 4.8 ml of 1,2-dimethoxyethane as solvent, 2,6-dimethyl-4-(2-methylthio-1-oxido-3-pyridyl)-1,4-dihydropyridine-3,5-dicarboxylic acid diethyl ester which, after recrystallisation from acetonitrile, melts at 222°–224°.

EXAMPLE 21

Analogously to the method described in Example 4 there is obtained from 13.7 g of 2-methylpyridine-3-carboxaldehyde-1-oxide, 17.4 g of acetoacetic acid isobutyl ester and 13.0 g of 3-aminocrotonic acid methyl ester in 100 ml of 1,2-dimethoxyethane as solvent, an ester mixture which is chromatographed over silica gel with ethyl acetate/hexane/methanol (10:20:5) as the liquid phase, and the eluates, which contain the main portion of the desired compound, are combined and concentrated by evaporation. After recrystallising the residue from ethanol and drying the crystals at 110° in a high vacuum, 2,6-dimethyl-4-(2-methyl-1-oxido-3-pyridyl)-1,4-dihydroxypyridine-3-carboxylic acid isobutyl ester 5-carboxylic acid methyl ester·⅓ ethanol is obtained, which melts at 220°–221° with decomposition.

EXAMPLE 22

A mixture of 4.0 g of 2-chloropyridine-3-carboxaldehyde-1-oxide, 3.3 g of 3-aminocrotonic acid ethyl ester and 4.12 g of 4-chloroacetoacetic acid ethyl ester in 80 ml of absolute ethanol is heated under reflux for 18 hours, the reaction mixture is cooled and the precipitated product is filtered with suction. The residue from filtration is washed with a large amount of water, dried and then recrystallised from a mixture of chloroform and methanol. The resulting 2-methyl-4-(1-oxido-2-chloro-3-pyridyl)-5-oxo-1,4,5,7-tetrahydrofuro[3,4-b]-pyridine-3-carboxylic acid ethyl ester melts at 235°–237°.

EXAMPLE 23

Analogously to the process described in Example 22 there is obtained from 6.5 g of 2-methylpyridine-3-carboxaldehyde-1-oxide, 6.1 g of 3-aminocrotonic acid ethyl ester and 7.75 g of 4-chloroacetoacetic acid ethyl ester in 100 ml of absolute ethanol, 2-methyl-4-(1-oxido-2-methyl-3-pyridyl)-5-oxo-1,4,5,7-tetrahydrofuro[3,4-b]-pyridine-3-carboxylic acid ethyl ester which, after recrystallisation from a mixture of methanol and methylene chloride, melts at 278° C.

EXAMPLE 24

Analogously to the process described in Example 22 there is obtained from 3.0 g of 2-methylmercaptopyridine-3-carboxaldehyde-1-oxide, 2.3 g of 3-aminocrotonic acid ethyl ester and 2.9 g of 4-chloroacetoacetic acid ethyl ester in 60 ml of absolute ethanol, 2-methyl-4-(1-oxido-2-methylthio-3-pyridyl)-5-oxo-1,4,5,7-tetrahydrofuro-[3,4-b]pyridine-3-carboxylic acid ethyl ester which, after recrystallisation from a mixture of methanol and methylene chloride, melts at 274°–278° C.

EXAMPLE 25

A mixture of 8.9 g of 2-methoxypyridine-3-carboxaldehyde-1-oxide, 14 ml of ethyl acetoacetate and 6 ml of 30% aqueous ammonia in 14 ml of 1,2-dimethoxyethane is stirred for 15 minutes at 20° C., then for 3.5 hours at a bath temperature of 90° C. The reaction mixture is then concentrated in vacuo, the residue is stirred with 10 ml of acetonitrile and the sparingly soluble components are filtered off with suction. The residue from filtration is recrystallised first from acetonitrile, then from 1,2-dimethoxyethane. The resulting 2,6-dimethyl-4-(1-oxido-2-methoxy-3-pyridyl)-1,4-dihydropyridine-3,5-dicarboxylic acid diethyl ester melts at 172°–174° C.

The 2-methoxypyridine-3-carboxaldehyde-1-oxide used as starting material can be obtained in the following manner: 14 g of 2-chloropyridine-3-carboxaldehyde-1-oxide [produced in accordance with Z. Chem., vol. 10, page 184 (1970)] are added to a solution of 5.53 g of sodium methoxide in 88 ml of absolute methanol and the mixture is heated for 3 hours at a bath temperature of 70° C. Subsequently, the reaction mixture is concentrated in vacuo, the residue is stirred thoroughly with methylene chloride and insoluble material is filtered off with suction by means of a filtering aid. The filtrate is concentrated by evaporation and the residue is twice extracted by boiling with ethyl acetate. The extracts are filtered, combined, and concentrated in vacuo. The resulting crude 2-methoxypyridine-3-carboxaldehyde-1-oxide is further processed as such.

EXAMPLE 26

Analogously to the process described in Example 1 there is obtained from 1.9 g of 2-methylsulphinylpyridine-3-carboxaldehyde-1-oxide, 3.1 ml of ethyl acetoacetate, 1.1 ml of 30% aqueous ammonia and 0.12 g of ammonium chloride in 3.1 ml of 1,2-dimethoxyethane, 2,6-dimethyl-4-(2-methylsulphinyl-1-oxido-3-pyridyl)-1,4-dihydropyridine-3,5-dicarboxylic acid diethyl ester which, after crystallisation from acetonitrile, melts at 220°–221° C. with the evolution of gas.

The 2-methylsulphinylpyridine-3-carboxaldehyde-1-oxide used as starting material and 10 mg of 4,4'-thiobis-(6-tert.-butyl-3-methylphenol) in 10 ml of chloroform are cooled to 0° and there is added dropwise to this a solution of 2.1 g of 3-chloroperbenzoic acid in 20 ml of chloroform. The mixture is left to stand overnight at 0° and then a further 0.2 g of 3-chloroperbenzoic acid is added. After one hour, 1.69 g of potassium carbonate are added to the cold reaction mixture, the mixture is stirred for one hour without being cooled and is then filtered with suction. The residue from filtration is washed with chloroform and the combined peroxide-free filtrates are concentrated to a volume of approximately 10 ml. The product is precipitated by the dropwise addition of ether, filtered with suction, washed with ether and yields 2-methylsulphinylpyridine-3-carboxaldehyde-1-oxide, which is further processed as such.

EXAMPLE 27

In an analogous manner, that is to say as described in the general description and illustrated in the foregoing Examples, it is possible by suitable choice of the starting materials and/or reaction conditions to obtain the following compounds:

6-hydroxymethyl-2-methyl-4-(1-oxide-3-pyridyl)-1,4-dihydropyridine-3,5-dicarboxylic acid diethyl ester, by the reaction of pyridine-3-carboxaldehyde-1-oxide, 3-aminocrotonic acid ethyl ester and 4,4-dimethoxyacetoacetic acid ethyl ester, cleavage of the dimethoxymethyl group in the resulting 6-dimethoxymethyl-2-methyl-4-(1-oxido-3-pyridyl)-1,4-dihydropyridine-3,5-dicarboxylic acid diethyl ester by treatment with hydrochloric acid, and reduction of the formyl group in 6-formyl-2-methyl-4-(1-oxido-3-pyridyl)-1,4-dihydropyridine-3,5-dicarboxylic acid diethyl ester by treatment with sodium borohydride;

6-cyanomethyl-2-methyl-4-(1-oxido-3-pyridyl)-1,4-dihydropyridine-3,5-dicarboxylic acid diethyl ester, by the reaction of 6-hydroxymethyl-2-methyl-4-(1-oxido-3-pyridyl)-1,4-dihydropyridine-3,5-dicarboxylic acid diethyl ester with thionyl chloride, and treatment of the resulting 6-chloromethyl-2-methyl-4-(1-oxido-3-pyridyl)-1,4-dihydropyridine-3,5-dicarboxylic acid diethyl ester with sodium cyanide;

6-cyano-2-methyl-4-(1-oxido-3-pyridyl)-1,4-dihydropyridine-3,5-dicarboxylic acid diethyl ester, by the reaction of 6-formyl-2-methyl-4-(1-oxido-3-pyridyl)-1,4-dihydropyridine-3,5-dicarboxylic acid diethyl ester with hydroxyamine hydrochloride and dehydration of the resulting 6-hydroxyiminomethyl-2-methyl-4-(1-oxido-3-pyridyl)-1,4-dihydropyridine-3,5-dicarboxylic acid diethyl ester by treatment with N,N'-dicyclohexyl carbodiimide;

6-ethoxycarbonyl-2-methyl-4-(1-oxido-3-pyridyl)-1,4-dihydropyridine-3,5-dicarboxylic acid diethyl ester, by the treatment of 6-cyanomethyl-2-methyl-4-(1- oxido-3-pyridyl)-1,4-dihydropyridine-3,5-dicarboxylic acid diethyl ester with ethanol in the presence of sulphuric acid and water;

6-ethoxycarbonylmethyl-2-methyl-4-(1-oxido-3-pyridyl)-1,4-dihydropyridine-3,5-dicarboxylic acid diethyl ester, by the reaction of pyridine-3-carboxaldehyde-1-oxide, 3-aminocrotonic acid ethyl ester and acetone-1,3-di-carboxylic acid diethyl ester;

6-(1-pyrrolidino)-2-methyl-4-(1-oxido-3-pyridyl)-1,4-dihydropyridine-3,5-dicarboxylic acid diethyl ester, by the reaction of pyridine-3-carboxaldehyde-1-oxide, ethyl acetoacetate and 2-(N,N-tetramethyleneamidino)-acetic acid ethyl ester;

6-[4-(2-oxo-1-imidazolidinyl)-1-piperidino]-2-methyl-4-(1-oxido-3-pyridyl)-1,4-dihydropyridine-3,5-dicarboxylic acid diethyl ester, by the reaction of pyridine-3-carboxaldehyde-1-oxide, ethyl acetoacetate and 3-imino-3-[4-(2-oxo-1-imidazolidinyl)-1-piperidino]-propionic acid ethyl ester;

6-[4-(2-furoyl)-1-piperazino]-2-methyl-4-(1-oxido-3-pyridyl)-1,4-dihydropyridine-3,5-dicarboxylic acid diethyl ester, by the reaction of pyridine-3-carboxaldehyde-1-oxide, ethyl acetoacetate and 3-imino-3-[4-(2-furoyl)-1-piperazino]-propionic acid ethyl ester;

6-[2-(4-morpholino)-ethyl]-2-methyl-4-(1-oxido-3-pyridyl)-1,4-dihydropyridine-3,5-dicarboxylic acid diethyl ester, by the treatment of 2,6-dimethyl-4-(1-oxido-3-pyridyl)-1,4-dihydropyridine-3,5-dicarboxylic acid diethyl ester with morpholine and paraformaldehyde;

6-(2-dimethylaminoethyl)-2-methyl-4-(1-oxido-3-pyridyl)-1,4-dihydropyridine-3,5-dicarboxylic acid diethyl ester, by the treatment of 2,6-dimethyl-4-(1-oxido-3-pyridyl)-1,4-dihydropyridine-3,5-dicarboxylic acid diethyl ester with dimethylamine and paraformaldehyde;

2,6-dimethyl-5-ethylsulphonyl-4-(1-oxido-3-pyridyl)-1,4-dihydropyridine-3-carboxylic acid ethyl ester, by the reaction of pyridine-3-carboxaldehyde-1-oxide, 3-aminocrotonic acid ethyl ester and 1-ethylsulphonyl acetone;

5-acetyl-2,6-dimethyl-4-(1-oxido-3-pyridyl)-1,4-dihydropyridine-3-carboxylic acid ethyl ester, by the reaction of pyridine-3-carboxaldehyde-1-oxide, 3-aminocrotonic acid ethyl ester and acetyl acetone;

6-hydroxymethyl-2-methyl-4-(1-oxido-2-methyl-3-pyridyl)-1,4-dihydropyridine-3,5-dicarboxylic acid diethyl ester, by the reaction of pyridine-3-carboxaldehyde-2-methyl-1-oxide, 3-aminocrotonic acid ethyl ester and 4,4-dimethoxyacetoacetic acid ethyl ester, cleavage of the dimethoxymethyl group in the resulting 6-dimethoxymethyl-2-methyl-4-(1-oxido-2-methyl-3-pyridyl)-1,4-dihydropyridine-3,5-dicarboxylic acid diethyl ester by treatment with hydrochloric acid, and reduction of the formyl group in the 6-formyl-2-methyl-4-(1-oxido-2-methyl-3-pyridyl)-1,4-dihydropyridine-3,5-dicarboxylic acid diethyl ester by treatment with sodium borohydride;

6-cyano-2-methyl-4-(1-oxido-2-methyl-3-pyridyl)-1,4-dihydropyridine-3,5-dicarboxylic acid diethyl ester, by the reaction of 6-formyl-2-methyl-4-(1-oxido-2-methyl-3-pyridyl)-1,4-dihydropyridine-3,5-dicarboxylic acid diethyl ester with hydroxylamine hydrochloride and dehydration of the resulting 6-hydroxyiminomethyl-2-methyl-4-(1-oxido-2-methyl-3-pyridyl)-1,4-dihydropyridine-3,5-dicarboxylic acid diethyl ester by treatment with N,N'-dicyclohexylcarbodiimide;

5-methyl-7-(1-oxido-3-pyridyl)-1,2,3,7-tetrahydroimidazo[1,2-a]pyridine-6,8-dicarboxylic acid diethyl ester of the formula

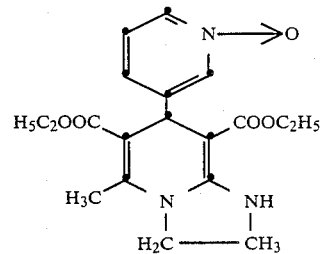

by the reaction of pyridine-3-carboxaldehyde-1-oxide, 2-(2-imidazolin-2-yl)-acetic acid ethyl ester and ethyl acetoacetate;

2-methyl-4-(1-oxido-2-methylsulphinyl-3-pyridyl)-5-oxo-1,4,5,7-tetrahydrofuro[3,4-b]pyridine-3-carboxylic acid ethyl ester, by the reaction of 2-methylsulphinyl-pyridine-3-carboxaldehyde-1-oxide, 3-aminocrotonic acid ethyl ester and 4-chloroacetoacetic acid ethyl ester in a suitable solvent, for example absolute ethanol, at elevated temperature;

2-methyl-4-(1-oxido-2-methylsulphonyl-3-pyridyl)-5-oxo-1,4,5,7-tetrahydrofuro[3,4-b]pyridine-3-carboxylic acid ethyl ester, by the reaction of 2-methylsulphonyl-pyridine-3-carboxaldehyde-1-oxide, 3-aminocrotonic acid ethyl ester and 4-chloroacetoacetic acid ethyl ester in a suitable solvent, for example absolute ethanol, at elevated temperature;

2-methyl-4-(1-oxido-2-methoxy-3-pyridyl)-5-oxo-1,4,5,7-tetrahydrofuro[3,4-b]pyridine-3-carboxylic acid ethyl ester, by the reaction of 2-methoxypyridine-3-carboxaldehyde-1-oxide, 3-aminocrotonic acid ethyl ester and 4-chloroacetoacetic acid ethyl ester in a suitable solvent, for example absolute ethanol, at elevated temperature;

2,6-dimethyl-4-(2-methylsulphonyl-1-oxido-3-pyridyl)-1,4-dihydropyridine-3,5-dicarboxylic acid diethyl ester, by the reaction of 2-methylsulphonylpyridine-3-carboxaldehyde-1-oxide, ethyl acetoacetate and aqueous ammonia in the presence of ammonium chloride.

EXAMPLE 28

Tablets containing 25 mg of 2,6-dimethyl-4-(1-oxido-3-pyridyl)-1,4-dihydropyridine-3,5-dicarboxylic acid diethyl ester can be produced in the following manner:

| Composition (for 1000 tablets) | |
| --- | --- |
| 2,6-dimethyl-4-(1-oxido-3-pyridyl)-1,4-dihydropyridine-3,5-dicarboxylic acid diethyl ester | 25.0 g |
| corn starch | 70.0 g |
| lactose (fine) | 78.5 g |
| cellulose (microcrystalline, granulated) | 75.0 g |
| magnesium stearate | 1.5 g |
| water | q.s. |

MANUFACTURE

The 2,6-dimethyl-4-(1-oxido-3-pyridyl)-1,4-dihydropyridine-3,5-dicarboxylic acid diethyl ester is mixed with 60 g of corn starch and the lactose, and kneaded with a paste produced from 10 g of corn starch and water. The moist mass is granulated, dried and mixed with the crystalline cellulose and the magnesium stearate. The homogeneous mixture is pressed to form 250 mg tablets (with a break groove) having a diameter of 9 mm.

EXAMPLE 29

Capsules containing 10 mg of active ingredient can be produced in the following manner:

COMPOSITION

| | |
|---|---|
| 2,6-dimethyl-4-(1-oxido-3-pyridyl)-1,4-dihydropyridine-3,5-dicarboxylic acid diethyl ester | 2500 mg |
| talcum | 200 mg |
| colloidal silica | 50 mg |

MANUFACTURE

The active ingredient is intimately mixed with the talcum and colloidal silica, the mixture is forced through a sieve having a mesh width of 0.5 mm, and filled in portions each of 11 mg into hard gelatin capsules of suitable size.

EXAMPLE 30

A sterile solution of 5.0 g of 2,6-dimethyl-4-(1-oxido-3-pyridyl)-1,4-dihydropyridine-3,5-dicarboxylic acid diethyl ester in 5000 ml of distilled water is filled into 5 ml ampoules which contain 5 mg of active ingredient in 5 ml of solution.

EXAMPLE 31

Instead of the compounds used as active ingredient in Examples 28 to 30, it is also possible to use the following compounds of the formula I, or pharmaceutically acceptable acid addition salts of such compounds with salt-forming basic groups, as active ingredients in tablets, dragées, capsules, ampoule solutions etc.: 2,6-dimethyl-4-(1-oxido-3-pyridyl)-1,4-dihydropyridine-3,5-dicarboxylic acid dimethyl ester; 2,6-dimethyl-4-(1-oxido-3-pyridyl)-1,4-dihydropyridine-3-carboxylic acid methyl ester 5-carboxylic acid ethyl ester; 2,6-dimethyl-4-(1-oxido-3-pyridyl)-1,4-dihydropyridine-3-carboxylic acid isobutyl ester 5-carboxylic acid methyl ester; 2,6-dimethyl-4-(2-methyl-1-oxido-6-pyridyl)-1,4-dihydropyridine-3,5-dicarboxylic acid diethyl ester; 2,6-dimethyl-1-[2-(4-morpholino)-ethyl]-4-(1-oxido-3-pyridyl)-1,4-dihydropyridine-3,5-dicarboxylic acid diethyl ester; 2,6-di-methyl-5-methylsulphonyl-4-(1-oxido-3-pyridyl)-1,4-di-hydropyridine-3-carboxylic acid methyl ester; 2-methyl-4-(1-oxido-3-pyridyl)-5-oxo-1,4,5,7-tetrahydro-furo[3,4-b]pyridine-3-carboxylic acid ethyl ester; 6-hydroxymethyl-2-methyl-5-methylaminocarbonyl-4-(1-oxido-3-pyridyl)-1,4-dihydropyridine-3-carboxylic acid ethyl ester; 2,6-dimethyl-4-(1-oxido-2-pyridyl)-1,4-dihydropyridine-3,5-dicarboxylic acid diethyl ester; 2,6-dimethyl-4-(1-oxido-4-pyridyl)-1,4-dihydropyridine-3,5-dicarboxylic acid diethyl ester; 2,6-dimethyl-4-(1-oxido-3-pyridyl)-1,4-dihydropyridine-3,5-dicarboxylic acid di-n-propyl ester; 2,6-dimethyl-4-(2-methyl-1-oxido-3-pyridyl)-1,4-dihydropyridine-3,5-dicarboxylic acid diethyl ester; 2,6-dimethyl-4-(2-chloro-1-oxido-3-pyridyl)-1,4-dihydropyridine-3,5-dicarboxylic acid diethyl ester; 2,6-dimethyl-4-(1-oxido-3-pyridyl)-1,4-dihydropyridine-3-carboxylic acid isopropyl ester 5-carboxylic acid (2-methoxyethyl)-ester; 2,6-dimethyl-4-(1-oxido-3-pyridyl)-1,4-dihydropyridine-3-carboxylic acid methyl ester 5-carboxylic acid [2-(N-methyl-N-benzylamino)-ethyl]-ester; 6-methoxymethyl-2-methyl-4-(1-oxido-3-pyridyl)-1,4-dihydropyridine-3-carboxylic acid ethyl ester 5-carboxylic acid methyl ester; 2-amino-6-methyl-4-(1-oxido-3-pyridyl)-1,4-dihydropyridine-3,5-dicarboxylic acid diethyl ester; 2,6-dimethyl-4-(2-methylthio-1-oxido-3-pyridyl)-1,4-dihydropyridine-3,5-dicarboxylic acid diethyl ester; 2,6-dimethyl-4-(2-methyl-1-oxido-3-pyridyl)-1,4-dihydropyridine-3-carboxylic acid isobutyl ester 5-carboxylic acid methyl ester; 6-hydroxymethyl-2-methyl-4-(1-oxido-2-methyl-3-pyridyl)-1,4-dihydropyridine-3,5-dicarboxylic acid diethyl ester; 6-cyano-2-methyl-4-(1-oxido-2-methyl-3-pyridyl)-1,4-dihydropyridine-3,5-dicarboxylic acid diethyl ester; 2-methyl-4-(1-oxido-2-chloro-3-pyridinyl)-5-oxo-1,4,5,7-tetrahydrofuro[3,4-b]pyridine-3-carboxylic acid ethyl ester, 2-methyl-4-(1-oxido-2-methyl-3-pyridinyl)-5-oxo-1,4,5,7-tetrahydrofuro[3,4-b]pyridine-3-carboxylic acid ethyl ester; 2-methyl-4-(1-oxido-2-methylthio-3-pyridinyl)-5-oxo-1,4,5,7-tetrahydrofuro[3,4-b]pyridine-3-carboxylic acid ethyl ester; 2-methyl-4-(1-oxido-2-methylsulphinyl-3-pyridinyl)-5-oxo-1,4,5,7-tetrahydrofuro[3,4-b]pyridine-3-carboxylic acid ethyl ester; 2-methyl-4-(1-oxido-2-methylsulphonyl-3-pyridinyl)-5-oxo-1,4,5,7-tetrahydrofuro[3,4-b]pyridine-3-carboxylic acid ethyl ester; 2,6-dimethyl-4-(1-oxido-2-methoxy-3-pyridyl)-1,4-dihydropyridine-3,5-dicarboxylic acid diethyl ester, 2,6-dimethyl-4-(2-methylsulphinyl-1-oxido-3-pyridyl)-1,4-dihydropyridine-3,5-dicarboxylic acid diethyl ester; and also the compounds of the formula I described in Example 27.

We claim:

1. A compound of the formula I

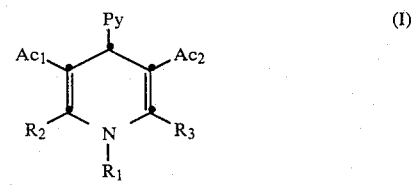

in which Py represents N-oxidopyridyl that is unsubstituted or substituted by lower alkyl, lower alkoxy, lower alkylthio, lower alkylsulphinyl, lower alkylsulphonyl and/or halogen, $R_1$ represents hydrogen, lower alkyl, di-lower alkylamino-lower alkyl, lower alkyleneamino-lower alkyl, morpholino-lower alkyl, thiomorpholino-lower alkyl, piperazino-lower alkyl or 4-lower alkyl-piperazino-lower alkyl, one of the radicals $R_2$ and $R_3$ represents lower alkyl and the other represents hydrogen, lower alkyl, hydroxy-lower alkyl, lower alkoxy-lower alkyl, gem-di-lower alkoxy-lower alkyl, halo-lower alkyl, oxo-lower alkyl, lower alkoxycarbonyl-lower alkyl, carbamoyl-lower alkyl, N-lower alkylcarbamoyl-lower alkyl, N,N-di-lower alkylcarbamoyl-lower alkyl, cyano-lower alkyl, amino-lower alkyl, lower alkylamino-lower alkyl, di-lower alkylamino-lower alkyl, lower alkyleneamino-lower alkyl, morpholino-lower alkyl, thiomorpholine-lower alkyl, piperazino-lower alkyl, 4-lower alkylpiperazino-lower alkyl, lower alkoxyimino-lower alkyl, in which lower alkoxy and imino substituents are attached to the same carbon atom, hydroxyimino-lower alkyl, lower alkoxyimino-lower alkyl, lower alkoxycarbonyl, carbamoyl, N-lower alkylcarbamoyl, N,N-di-lower alkylcarbamoyl, cyano, amino, lower alkylamino, di-lower alkylamino-lower alkylamino, lower alkyleneamino-lower alkylamino, morpholino-lower alkylamino, di-lower alkylamino, lower alkyleneamino, (2-oxo-1-imidazolidinyl)-lower alkyleneamino, morpholino, thiomorpholino, piperazino, 4-lower alkylpiperazino, 4-lower alkanoylpiperazino, 4-benzoylpiperazino, 4-furoylpiperazino or 4-thienoylpiperazino, it being possible for an amino group $R_2$ or $R_3$ also to be bonded to a lower alkyl radical $R_1$ and to form together with that radical a 1-aza-lower alkylene radical the nitrogen atom of which is bonded to the 2- or 6-ring carbon atom of the 1,4-dihydropyridine ring, or, if $R_2$ or $R_3$ represents hydroxy-lower alkyl, for this hydroxy-lower alkyl, together with the adjacent acyl radical $Ac_1$ or $Ac_2$, to form a 2-oxa-1-oxo-lower alkylene radical, the carbonyl group of which is bonded to the 3- or 5-ring carbon atom of the 1,4-dihydropyridine ring, and each of the radicals $Ac_1$ and $Ac_2$, independently of the other, represents lower alkanoyl, benzoyl that is unsubstituted or substituted by lower alkyl, lower alkoxy and/or halogen, lower alkylsulphonyl, phenylsulphonyl that is unsubstituted or substituted by lower alkyl, lower alkoxy and/or halogen, lower alkoxycarbonyl, hydroxy-lower alkoxycarbonyl, lower alkoxy-lower alkoxycarbonyl, amino-lower alkoxycarbonyl, lower alkylamino-lower alkoxycarbonyl, di-lower alkylamino-lower alkoxycarbonyl, N-lower alkyl-N-phenyl-lower alkylamino-lower alkoxycarbonyl, lower alkyleneamino-lower alkoxycarbonyl, morpholino-lower alkoxycarbonyl, thiomorpholino-lower alkoxycarbonyl, piperazino-lower alkoxycarbonyl, 4-lower alkylpiperazino-lower alkoxycarbonyl, phenyl-lower alkoxycarbonyl that is unsubstituted or substituted by lower alkyl, lower alkoxy and/or halogen carbamoyl, N-lower alkylcarbamoyl, N,N-di-lower alkylcarbamoyl, N,N-lower alkylenecarbamoyl, morpholinocarbonyl, thiomorpholinocarbonyl, piperazinocarbonyl or 4-lower alkylpiperazinocarbonyl, or salts of such compounds having salt-forming groups.

2. A compound of the formula I according to claim 1, in which Py, $R_1$, $Ac_1$ and $Ac_2$ have the meanings given in claim 3, and one of the radicals $R_2$ and $R_3$ represents lower alkyl and the other represents hydrogen, lower alkyl, hydroxy-lower alkyl, lower alkoxy-lower alkyl, halo-lower alkyl, lower alkoxycarbonyl-lower alkyl, carbamoyl-lower alkyl, N-lower alkylcarbamoyl-lower alkyl, N,N-di-lower alkylcarbamoyl-lower alkyl, cyano-lower alkyl, amino-lower alkyl, lower alkylamino-lower alkyl, di-lower alkylamino-lower alkyl, lower alkyleneamino-lower alkyl, morpholino-lower alkyl, thiomorpholino-lower alkyl, piperazino-lower alkyl, 4-lower alkylpiperazino-lower alkyl, lower alkoxycarbonyl, carbamoyl, N-lower alkylcarbamoyl, N,N-di-lower alkylcarbamoyl, cyano, amino, lower alkylamino, di-lower alkylamino-lower alkylamino, lower alkyleneamino-lower alkylamino, morpholino-lower alkylamino, di-lower alkylamino, lower alkyleneamino, (2-oxo-1-imidazolidinyl)-lower alkyleneamino, morpholino, thiomorpholino, piperazino, 4-lower alkylpiperazino, 4-lower alkanoylpiperazino, 4-benzoylpiperazino, 4-furoylpiperazino or 4-thienoylpiperazino, it being possible for an amino group $R_2$ or $R_3$ also to be bonded to a lower alkyl radical $R_1$ and to form together with that radical a 1-aza-lower alkylene radical the nitrogen atom of which is bonded to the 2- or 6-ring carbon atom of the 1,4-dihydropyridine ring, or, if $R_2$ or $R_3$ represents, for example, hydroxy-lower alkyl, for this hydroxy-lower alkyl, together with the adjacent acyl radical $Ac_1$ or $Ac_2$, to form a 2-oxa-1-oxo-lower alkylene radical the carbonyl group of which is bonded to the 3- or 5-ring carbon atom of the 1,4-dihydropyridine ring, or salts of such compounds having salt-forming groups.

3. A compound of the formula I according to claim 1, in which Py represents N-oxidopyridyl that is unsubstituted or substituted by lower alkyl or lower alkylsulphinyl, $R_1$ represents hydrogen, lower alkyl, 2-di-lower alkylamino-lower alkyl, 2-lower alkyleneamino-lower alkyl or 2-(4-morpholino)-lower alkyl, one of the radicals $R_2$ and $R_3$ represents lower alkyl and the other represents hydrogen, lower alkyl, hydroxy-lower alkyl, halo-lower alkyl, lower alkoxycarbonyl-lower alkyl, cyano-lower alkyl, di-lower alkylamino-lower alkyl, lower alkoxycarbonyl, cyano, amino, (4-morpholino)-lower alkylamino, lower alkyleneamino, (2-oxo-1-imidazolidinyl)-lower alkyleneamino or 4-(2-furoyl)-piperazino, it being possible for an amino group $R_2$ or $R_3$ to be bonded to a lower alkyl radical $R_1$ and to form together with that radical a 1-aza-lower alkylene radical, the aza nitrogen atom of which is bonded to the 2- or 6-ring carbon atom of the 1,4-dihydropyridine ring, or, if $R_2$ or $R_3$ represents, for example, hydroxy-lower alkyl, for this hydroxy-lower alkyl, together with the adjacent acyl radical $Ac_1$ or $Ac_2$, to form a 2-oxa-1-oxo-lower alkylene radical, the carbonyl group of which is bonded to the 3- or 5-ring carbon atom of the 1,4-dihydropyridine ring, and each of the radicals $Ac_1$ and $Ac_2$, independently of the other, represents lower alkanoyl, lower alkylsulphonyl, lower alkoxycarbonyl, hydroxy-lower alkoxycarbonyl, lower alkoxy-lower alkoxycarbonyl, di-lower alkylamino-lower alkoxycarbonyl, N-lower alkyl-N-phenyl-lower alkylamino-lower alkoxycarbonyl, lower alkyleneamino-lower alkoxycarbonyl, (4-morpholino)-lower alkoxycarbonyl, carbamoyl, N-lower alkylcarbamoyl, N,N-di-lower alkylcarbamoyl, N,N-lower alkylenecarbamoyl or 4-morpholinocarbonyl, wherein lower alkyl, lower alkoxy and lower alkanoyl contain up to and including 4 carbon atoms, lower alkylene contains 4 or 5 chain carbon atoms, 1-aza-lower alkylene contains 2 or 3 chain carbon atoms, and 2-oxa-1-oxo-lower alkylene contains 2 chain carbon atoms, or salts of such compounds having salt-forming groups.

4. A compound of the formula I according to claim 1, in which Py represents N-oxidopyridyl, $R_1$ represents hydrogen, lower alkyl, 2-(di-lower alkylamino)-lower alkyl, 2-(lower alkyleneamino)-lower alkyl, or 2-(4-morpholino)-lower alkyl, one of the radicals $R_2$ and $R_3$ represents lower alkyl, and the other represents lower alkyl, hydroxy-lower alkyl, halo-lower alkyl, 2-(di-lower alkylamino)-lower alkyl, lower alkoxycarbonyl, cyano, amino, (4-morpholino)-lower alkylamino, lower alkyleneamino, (2-oxo-1-imidazolidinyl)-lower alkyleneamino, or 4-(2-furoyl)-piperazino, it being possible for an amino group $R_2$ or $R_3$ to be bonded to a lower alkyl radical $R_1$ and, together with that radical, to form a 1-aza-lower alkylene radical, the aza nitrogen atom of which is bonded to the 2- or 6-ring carbon atom of the 1,4-dihydropyridine ring, or, if $R_2$ or $R_3$ represents, for example, hydroxy-lower alkyl, for this hydroxy-lower alkyl, together with the adjacent acyl radical $Ac_1$ or $Ac_2$, to form a 2-oxa-1-oxo-lower alkylene radical, the carbonyl group of which is bonded to the 3- or 5-ring carbon atom of the 1,4-dihydropyridine ring, and each of the radicals $Ac_1$ and $Ac_2$, independently of the other, represents lower alkanoyl, lower alkylsulphonyl, lower alkoxycarbonyl, 2-lower alkoxy-lower alkoxycarbonyl, di-lower alkylamino-lower alkoxycarbonyl, or N-lower alkyl-N-phenyl-lower alkylamino-lower alkoxycarbonyl, carbamoyl, N-lower alkylcarbamoyl, N,N-di-lower alkylcarbamoyl, or 4-morpholinocarbonyl, wherein lower alkyl, lower alkoxy and lower alkanoyl contain up to and including 4 carbon atoms, lower alkylene contains 4 or 5 chain carbon atoms, 1-aza-lower alkylene contains 2 or 3 chain carbon atoms and 2-oxa-1-oxo-lower alkylene contains 2 chain carbon atoms, or salts of such compounds having salt-forming basic groups.

5. A compound of formula I according to claim 1, in which Py represents N-oxidopyridyl, $R_1$ represents hydrogen or 2-(4-morpholino)-ethyl, one of the radicals $R_2$ and $R_3$ represents methyl and the other represents methyl, hydroxymethyl, lower alkoxycarbonyl, cyano or amino, and each of the radicals $Ac_1$ and $Ac_2$, independently of the other, represents lower alkanoyl, lower alkylsulphonyl, lower alkoxycarbonyl, carbamoyl, N-lower alkylcarbamoyl, or N,N-di-lower alkylcarbamoyl, wherein lower alkyl, lower alkoxy and lower alkanoyl contain up to and including 4 carbon atoms, or salts of such compounds having salt-forming basic groups.

6. A compound according to claim 1 which is 2,6-dimethyl-4-(1-oxido-3-pyridyl)-1,4-dihydropyridine-3,5-dicarboxylic acid diethyl ester.

7. A compound as claimed in claim 1, which is 2,6-dimethyl-4-(2-methyl-1-oxido-3-pyridyl)-1,4-dihydropyridine-3,5-dicarboxylic acid diethyl ester.

8. A compound as claimed in claim 1, which is 2,6-dimethyl-4-(2-methylthio-1-oxido-3-pyridyl)-1,4-dihydropyridine-3,5-dicarboxylic acid diethyl ester.

9. A pharmaceutical composition useful as antihypertensive agent and coronary dilator in the treatment of cardiovascular conditions such as high blood pressure, vascular constrictions, Angina pectoris and its sequelae and cardiac insufficiency comprising a therapeutically effective amount of a compound of the formula I as claimed in claim 1 with the exception of those in which $R_2$ or $R_3$ represents hydroxy-lower alkyl and this hydroxy-lower alkyl, together with the adjacent acyl radical $Ac_1$ or $Ac_2$ forms a 2-oxa-1-oxo-lower alkylene radical, the carbonyl group of which is bonded to the 3- or 5-ring carbon atom of the 1,4-dihydropyridine ring, or a pharmaceutically acceptable acid addition salt of such compound having salt-forming groups together with a pharmaceutically acceptable excipient.

10. A pharmaceutical composition useful for an increase in the myocardial contractility in the treatment of cardiac insufficiency comprising a therapeutically effective amount of a compound of the formula I as claimed in claim 1, in which $R_2$ or $R_3$ represents hydroxy-lower alkyl, and this hydroxy-lower alkyl together with the adjacent acyl radical $Ac_1$ or $Ac_2$ forms a 2-oxa-1-oxo-lower alkylene radical the carbonyl group of which is bonded to the 3- or 5-ring carbon atom of the 1,4-dihydropyridine ring, or a pharmaceutically acceptable acid addition salt of such compound having salt-forming groups together with a pharmaceutically acceptable excipient.

11. A method for the treatment of cardiovascular conditions such as high blood pressure, vascular constrictions, Angina pectoris and its sequelae and cardiac insufficiency which comprises administering of a therapeutically effective amount of a compound of the formula I as claimed in claim 1, with the exception of those in which $R_2$ or $R_3$ represents hydroxy-lower alkyl, and this hydroxy-lower alkyl together with the adjacent acyl radical $Ac_1$ or $Ac_2$ forms a 2-oxa-1-oxo-lower alkylene radical, the carbonyl group of which is bonded to the 3- or 5-ring carbon atom of the 1,4-dihydropyridine ring, or a pharmaceutically acceptable acid addition salt of such compound having salt-forming groups, to a host in need thereof.

12. A method for an increase in the myocardial contractility in the treatment of cardiac insufficiency which comprises administering of a therapeutically effective amount of a compound of the formula I as claimed in claim 1, in which $R_2$ or $R_3$ represents hydroxy-lower alkyl, and this hydroxy-lower alkyl together with the adjacent acyl radical $Ac_1$ or $Ac_2$ forms a 2-oxa-1-oxo-lower alkylene radical the carbonyl group of which is bonded to the 3- or 5-ring carbon atom of the 1,4-dihydropyridine ring, or a pharmaceutically acceptable acid addition salt of such compound having salt-forming groups, to a host in need thereof.

* * * * *